United States Patent
Takaku et al.

(10) Patent No.: US 6,291,432 B1
(45) Date of Patent: Sep. 18, 2001

(54) TRIPEPTIDE COMPOUNDS AND ANTI-AIDS MEDICINE

(75) Inventors: Haruo Takaku; Satoshi Nojima, both of Urawa; Tsutomu Mimoto, Toda; Keisuke Terashima, Yono; Yoshiaki Kiso, Ibaraki, all of (JP)

(73) Assignee: Japan Energy Corporation, Tokyo (JP)

(*) Notice: Subject to any disclaimer, the term of this patent is extended or adjusted under 35 U.S.C. 154(b) by 0 days.

(21) Appl. No.: 09/155,773

(22) PCT Filed: Dec. 22, 1997

(86) PCT No.: PCT/JP97/04734

§ 371 Date: Feb. 16, 1999

§ 102(e) Date: Feb. 16, 1999

(87) PCT Pub. No.: WO98/29118

PCT Pub. Date: Jul. 9, 1998

(30) Foreign Application Priority Data

Dec. 27, 1996 (JP) .................................................. 8-359226
May 23, 1997 (JP) .................................................. 9-150520

(51) Int. Cl.[7] .......................... A61K 38/06; A61K 38/07; C07K 9/00
(52) U.S. Cl. ............................ 514/18; 514/2; 514/19; 530/300; 530/331; 424/185.1
(58) Field of Search ................... 514/2.15, 19; 530/300, 530/331; 424/155.1

(56) References Cited

U.S. PATENT DOCUMENTS

| | | | |
|---|---|---|---|
| 4,963,655 | 10/1990 | Kinder et al. | 530/331 |
| 5,086,165 | 2/1992 | Marshall et al. | 530/329 |
| 5,126,326 | 6/1992 | Anderson et al. | 514/17 |
| 5,132,400 | 7/1992 | Gammill et al. | 530/317 |
| 5,145,951 | 9/1992 | Voges et al. | 530/330 |
| 5,187,074 | 2/1993 | Treiber et al. | 435/41 |
| 5,188,950 | 2/1993 | Balani et al. | 435/120 |
| 5,192,668 | 3/1993 | Treiber et al. | 435/41 |
| 5,212,157 | 5/1993 | Anderson et al. | 514/17 |
| 5,342,922 | 8/1994 | Marshall et al. | 530/329 |
| 5,434,265 | 7/1995 | Fritz et al. | 546/146 |
| 5,438,118 | 8/1995 | Callahan et al. | 530/330 |
| 5,475,013 | 12/1995 | Talley et al. | 514/311 |
| 5,476,874 | 12/1995 | Hungate et al. | 514/599 |
| 5,491,166 | 2/1996 | Kaldor et al. | 514/481 |
| 5,492,910 | 2/1996 | Barrish et al. | 514/237.5 |
| 5,502,060 | 3/1996 | Thompson et al. | 514/307 |
| 5,502,061 | 3/1996 | Hui et al. | 514/311 |
| 5,514,802 | 5/1996 | Fritz et al. | 546/146 |
| 5,644,028 | 7/1997 | Mimoto et al. | 530/331 |

FOREIGN PATENT DOCUMENTS

| | | | |
|---|---|---|---|
| 0 394 853 | 10/1990 | (EP) | C07K/5/06 |
| 0 438 311 A2 | 7/1991 | (EP) | C07K/5/02 |
| 0 490 667 A2 | 6/1992 | (EP) | C07K/5/02 |
| 0498680 * | 8/1992 | (EP) . | |
| 0 498 680 A1 | 8/1992 | (EP) | C07D/207/16 |
| 0587311A1 | 3/1994 | (EP) . | |
| 0 604 184 A1 | 6/1994 | (EP) | C07C/323/60 |
| 0 604 185 A1 | 6/1994 | (EP) | C07D/217/26 |
| 05294993A | 10/1991 | (JP) . | |
| 05178824A | 6/1992 | (JP) . | |
| 06220031 * | 8/1994 | (JP) . | |
| 10-25242 * | 5/1996 | (JP) . | |
| WO92/03472 | 3/1992 | (WO) | C07K/5/06 |
| WO93/02057 | 2/1993 | (WO) | C07D/233/64 |
| WO93/13066 | 7/1993 | (WO) . | |
| WO94/18192 | 8/1994 | (WO) | C07D/401/14 |
| WO94/26749 | 11/1994 | (WO) | C07D/493/04 |
| WO95/14655 | 6/1995 | (WO) | C07C/219/02 |
| WO 96/28423 | 9/1996 | (WO) . | |

OTHER PUBLICATIONS

N.A. Roberts et al., "Rational Design of Peptide–Based HIV Protease Inhibitors" *Science* 248:358–362.

T. Robbins et al., "HIV Protease Inhibitors: Their Anti–HIV Activity and Potential Role in Treatment" *J. Acquired Immune Deficiency Syndromes* 6(2):162–170 (1993).

Communications to the Editor, "Intriguing Structure—Activity Relations Underlie the Potent Inhibition of HIV Protease by Norstatine–Based Peptides" *J. Med. Chem.* 35:1318–1320 (1992).

Baldwin et al. (1995), "Structure of HIV–1 Protease With KNI–272, A Tight–Binding Transition–State Analog Containing Allophenylnorstatine," 3 *Structure* 581–590.

Kiso (1995), "Design and Synthesis of HIV Protease Inhibitors Containing Allophenylnorstatine As A Transition–State Mimic," *Aspartic Proteinases Structure, Function, Biology and Biomedical Implications*, Ed. Kenji Takahashi, Plenum Press, NY, pp. 413–423.

(List continued on next page.)

*Primary Examiner*—Bennett Celsa
(74) *Attorney, Agent, or Firm*—Testa Hurwitz & Thibeault, LLP

(57) ABSTRACT

A novel tripeptide compound represented by the following general formula (I) exhibiting superior HIV protease inhibition activity, and an anti-AIDS medicine comprising this compound as an effective component and a pharmaceutically acceptable salt thereof.

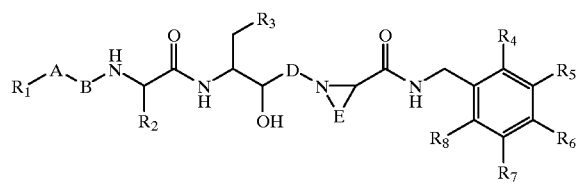

(I)

(R)-N-(2-methylbenzyl)-3-{(2S,3S)-3-[N-(2-chromonecarbonyl)-L-asparaginyl]amino-2-hydroxy-4-phenylbutanoyl}-5,5-dimethyl-1,3-thiazolidine-4-carboxamide can be given as a typical example of this compound.

23 Claims, No Drawings

OTHER PUBLICATIONS

Gulnik et. al. (1995), "Kinetic Characterization and Cross–Resistance Patterns of HIV–1 Protease Mutant Selected under Drug Pressuer," *Biochemistry*, vol. 34, No. 29, 9282–9287.

Kageyama et al. (1993), "In Vitro Anti–Human Immunodeficiency Virus (HIV) Activities of Transition State Mimetic HIV Protease Inhibitors Containing Allophenylnorstatine," 37 *Antimicrob. Agents & Chemo.* 4:810–817.

Humphrey et al. (1997), "Removal of Human Immunodeficiency Virus Type I (HIV–1) Protease Inhibitors From Preparations of Immature HIV–1 Virions Does Not Result in an Increase in Infectivity or the Appearance of Mature Morphology," 41 *Antimicrob. Agents & Chemo.* 5:1017–1023.

Uchida et al. (1997), "HIV–1 Protease Does Not Play A Critical Role In The Early Stages of HIV–1 Infection," 36 *Antiviral Research* 107–113.

Fahey et al., "Status of Immune–Based Therapies In HIV Infection And AIDS," *Clin. Exp. Immunol.*, 88:1–5 (1992).

Fox, J.L., "No Winners Against AIDS," *Bio/Technology*, 12:128 (Feb., 1994).

Haynes et al., "Update On The Issues Of HIV Vaccine Development," *Ann. Med.*, 28:39–41 (1996).

Ashorn et al. (1990), "An Inhibitor of the Protease Blocks Maturation of Human and Simian Immunodeficiency Viruses and Spread of Infection," 87 *Proc. Natl. Acad. Sci. USA* 7472–7476.

Debouck et al. (1990), "Human Immunodeficiency Virus Protease: A Target For AIDS Therapy," 21 *Drug Dev. Res.* 1–17.

Meek et al. (1990), "Inhibition of HIV–1 Protease In Infected T–lymphocytes by Synthetic Peptide Analogues," 343 *Nature* 90–92.

McCune et al. (1990), "Suppression of HIV Infection in AZT–Treated SCID–hu Mice," 247 *Science* 564–566.

Kaneshima et al. (1991), "Human Immunodeficiency Virus Infection of Human Lymph Nodes in the SCID–hu Mouse," 88 *Proc. Natl. Acad. Sci. USA* 4523–4527.

McCune et al. (1991), "Preclinical Evaluation of Human Hematolymphoid Function in the SCID–hu Mouse," 124 *Immunolog. Rev.* 45–62.

Mimoto et al. (1991), "Rational Design and Synthesis of a Novel Class of Active Site–Targeted HIV Protease Inhibitors Containing a Hydroxymethylcarbonyl Isostere. Use of Phenylnorstatine or Allophenylnorstatine As A Transition–State Mimic," 39 *Chem. Pharm. Bull.* 9:2465–2467.

Romero et al. (1991), "Nonnucleoside Reverse Transcriptase Inhibitors That Potently and Specifically Block Human Immunodeficiency Virus Type 1 Replication," 88 *Proc. Natl. Acad. Sci. USA* 8806–8810.

Shih et al. (1991), "Postexposure Prophylaxis With Zidovudine Suppresses Human Immunodeficiency Virus Type 1 Infection in SCID–hum Mice in a Time–Dependent Manner," 163 *J. Infect. Dis.* 625–627.

Kageyama et al. (1992), "In Vitro Inhibition of Human Immunodeficiency Virus (HIV) Type 1 Replication by $C_2$ Symmetry–Based HIV Protease Inhibitors As Single Agents or in Combination," 36 *Antimicrob. Agents Chem.* 5:926–931.

Meek (1992), "Inhibitors of HIV–1 Protease," 6 *J. Enzyme Inhib.* 65–98.

Mimoto et al. (1992), "Kynostatin (KNI)–227 and –272, Highly Potent Anti–HIV Agents: Conformationally Constrained Tripeptide Inhibitors of HIV Protease Containing Allophenylnorstatine," 40 *Chem. Pharm. Bull.* *:2251–2253.

"Japan Energy To Test AIDS Drug In Britain," Press Release Dec. 4, 1995; Jiji Press Ticker Service, Tokyo, Japan.

"Japan Energy Starts Clinical Testing of AIDS Drug In UK," Press Release Dec. 5, 1995; Jiji Press Ticker Service, Tokyo, Japan.

"Anti–AIDS Drug Test Go To Britain," Press Release Dec. 5, 1995; *Japan Times*, Tokyo, Japan.

Ussery et al. (1995), "In Vivo Antibacterial of the Protease Inhibitors KNI–272 in the HIV–Infected HuPBMC–SCID Mouse Model," 35th Interscience Conference on Antimicrobial Agents and Chemotherapy, Annual Meeting of The American Society For Microbiology, Abstract No. 125, p. 227.

Abstract, "XI International Conference on AIDS, Vancouver, Jul. 7–12, 1996," vol. 1, p. 77 (Ref. No. Mo.B. 1132); published Jul. 6, 1996; presented Jul. 8, 1996.

Caplus AN 1993: 22632, 1993.*

* cited by examiner

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:synthesized
      peptide substrate
<220> FEATURE:
<223> OTHER INFORMATION: wherein the Xaa at position 6 represents
      4-nitro-phenylalanine and wherein the Xaa at
      position 9 represents
      -NH-CH(CH2-CH2-CH2-CH3)-CONH2

<400> SEQUENCE: 1

Lys Ala Arg Val Tyr Xaa Glu Ala Xaa
 1               5
```

TRIPEPTIDE COMPOUNDS AND ANTI-AIDS MEDICINE

RELATED APPLICATIONS

This application claims the benefit of priority to International Application Serial No. PCT/JP97/04734 filed on Dec. 22, 1997 and Japanese Application Serial Nos. 8/359226 filed on Dec. 27, 1996 and 9/150520 filed on May 23, 1997.

FIELD OF TECHNOLOGY

The present invention relates to a novel tripeptide compounds exhibiting an action to inhibit an enzymatic activity of a protease which originates from human immunodeficiency virus (HIV). Moreover, the present invention relates to an anti-AIDS medicine which can control in vivo growth of HIV utilizing the inhibitive activity of this novel tripeptide compound against protease originating from HIV.

BACKGROUND OF THE INVENTION

Human immunodeficiency virus (HIV) which causes AIDS produces precursor proteins such as a reverse transcriptase or Gag protein used for production of the virus particles in host cells. These precursor proteins can exhibit their functions only when cut into a specific size by a protease of a virus origin (HIV protease). The HIV protease inhibitor which blocks formation and growth of infectious virus particles by inhibiting the enzymatic activity of the HIV protease can be used as an anti-virus agent. Several HIV protease inhibitors have already been reported. One of them is a transition state mimetic which is a compound something like a synthetic peptide (see, for example, T. Robins, J. Plattner, J. Acquir. Immun. Defic. Syndr., 6, 162 (1993)). For example, a hydroxyethylamine derivative such as Ro31-8959 (N. A. Roberts et al., Science 248, 358–361 (1990)) which contains a phenylalanine $\phi[CH(OH)CH_2N]$ decahydroisoquinolinecarboxylic acid skeleton similar to an amino acid sequence which is selectively cleaved by an HIV protease, such as -Tyr . . . Pro or -Phe . . . Pro, and a hydroxymethylcarboxamide derivative such as a peptide derivative including a norstati skeleton such as phenylalanine $\phi[CH(OH)C(O)N]$proline (T. F. Tam et al., J. Med. Chem. 35, 1318–1320 (1992)) are useful as an HIV protease inhibitor. Clinical application of these substances is being actively promoted.

Specifically, like a transition state mimetic these compounds utilize an HIV protease inhibition activity to control production of the virus particles in host cells, whereby growth and infection of HIV can be controlled and AIDS can be prevented. Clinical application of these compounds as the anti-AIDS medicines is being adopted (Nakajima et al., The Pharmaceuticals monthly, Vol. 35, 2983–2989 (1993)). These transition state mimetics are expected to become next generation anti-AIDS medicines succeeding nucleic acid derivative-type reverse transcriptase inhibitors such as AZT (azidothymidine), DDC (dideoxycytidine), and DDI (dideoxyinosine) which are already clinically used as anti-AIDS drugs.

The present inventors have also discovered that a group of synthetic peptide compounds which are transition state mimetics including a 3-amino-2-hydroxy-4-phenylbutanoic acid residue exhibit a strong HIV protease inhibitive action and are useful as anti-AIDS medicines. The inventors have filed a patent application relating to the HIV protease inhibitor (Japanese Patent Application Laid-open No. 170722/1993). The inventors of the present invention continued the studies in which the inventors have synthesized various peptide compounds and determined chemical structures of novel compounds, including novel compounds exhibiting superior inhibition activity against HIV protease (Japanese Patent Application Laid-open No. 185631/1996, European Patent Publication EP 751145 A2).

However, hydroxymethylcarboxamide derivatives having superior HIV protease inhibition activity among these peptide-type compounds require a comparatively high dose to clinically exhibit a certain effect in many cases. Because anti-AIDS medicines are continuously administered for a long period of time, development of a compound possessing a high HIV protease inhibition activity which can provide a certain effect by oral administration at a small dose is desired. Specifically, development of a compound possessing a novel structure which is capable of tightly binding with HIV protease and exhibits a high treatment effect at a lower plasma concentration is desired.

DISCLOSURE OF THE INVENTION

The present invention was completed in view of this situation and has an object of providing a novel tripeptide compound showing a high HIV protease inhibition activity as compared with an HIV protease inhibitor consisting of a transition-state mimetic peptide compound which has been proposed as a conventional anti-AIDS medicine and exhibiting superior anti-HIV virus activity accompanied by this high HIV protease inhibition activity. Another object of the present invention is to provide an anti-AIDS medicine comprising this novel tripeptide compound as an active component and exhibiting a treatment effect with a smaller dose.

In an effort to solve these problems, the present inventors have made extensive improvement in conventional transition-state mimetic substance and, as a result, the inventors have designed and prepared a novel tripeptide compound. More specifically, the inventors of the present invention have found that a tripeptide compound having a skeleton similar to an amino acid sequence which is selectively cleared by an HIV protease, such as -Tyr . . . Pro or -Phe . . . Pro, particularly a hydroxymethylcarbamide derivative including a norstatin skeleton such as phenylalanine $\phi[(CH(OH)C(O)N]$ proline, or a hydroxyethylamine derivative including phenylalanine $\phi[CH(OH)CH_2N]$ decahydroisoquinolinecarboxylic acid, exhibits a high HIV protease inhibition activity and a high action of suppressing growth of HIV viruses, particularly when a novel structure is introduced in the C-terminal amide structure. This finding has led to the completion of the present invention. The inventors have further found that another novel tripeptide produced by replacing a substitution group on the N-terminal amino group with an acyl group having a specific structure exhibits a high HIV protease inhibition activity and a high action of suppressing growth of HIV viruses. This finding has led to the completion of another feature of the present invention.

The above object can be achieved in the present invention by a novel tripeptide compound represented by the following formula (I), (I)

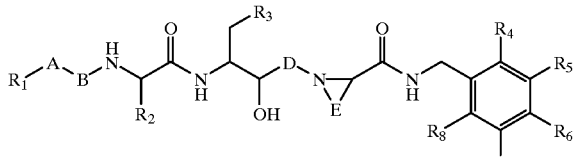

wherein A is —NH—, —NR— (wherein R represents an alkyl group having 6 or less carbon atoms), —O—CH$_2$—, —CH$_2$—O— or a single bond; B is —CO— or —SO$_2$—; D is —CO— or —CH$_2$—; E represents a divalent hydrocarbon group which may form a 5 to 7 member ring together with the adjacent nitrogen atom and carbon atom or a divalent hydrocarbon group with one or more carbon atoms therein being replaced by one or more hetero atoms, wherein said ring may form a condensed ring together with another 5 to 7 member ring or may have 3 or less substituents on that ring; $R_1$ is a hydrogen atom, an alkyl group having 6 or less carbon atoms, or an aromatic group or heterocyclic group having 10 or less carbon atoms, wherein the said alkyl group may possess an alkyloxy group having 4 or less carbon atoms as an substituent, said aromatic group or heterocyclic group may be substituted by an alkyl group having 4 or less carbon atoms, alkyloxy group, mono or dialkyl-substituted amino group, halogeno group, hydroxyl group, amino group, or an alkyl or alkenyl group having 3 or less carbon atoms which may be substituted by a monocyclic aromatic group or monocyclic heteroaromatic group; $R_2$ is an aliphatic hydrocarbon group having 1–7 carbon atoms or an aromatic hydrocarbon group, provided that the aliphatic hydrocarbon group may have either a linear or branched structure and the carbon atom forming the skeleton of said aliphatic hydrocarbon group or aromatic hydrocarbon group may be replaced by a hetero atom, or the hydrogen atom thereon may be substituted by a carbamoyl group, carboxyl group or halogeno group; $R_3$ is an aryl group, arylthio group or aryloxy group, and may contain a substituent on the aromatic ring; and $R_4$, $R_5$, $R_6$, $R_7$, and $R_8$ respectively represent a hydrogen atom, alkyl group having 3 or less carbon atoms, halogeno group, amino group, hydroxyl group, aminomethyl group, hydroxymethyl group, or an amino group substituted by one or two (mono or di) alkyl group having 3 or less carbon atoms; or a pharmaceutically acceptable salt thereof.

The above object can be further achieved in the present invention by an anti-AIDS medicine comprising as an effective component a novel tripeptide compound of the following formula (II), (II)

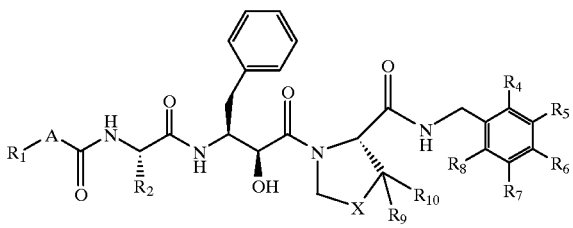

wherein A, $R_1$, $R_2$, $R_4$, $R_5$, $R_6$, $R_7$, and $R_8$ are the same as defined for the formula (I), X is an oxygen atom or sulfur atom, $R_9$ and $R_{10}$ respectively represents a hydrogen atom or a linear or branched aliphatic hydrocarbon group having 1–6 carbon atoms, or a pharmaceutically acceptable salt thereof.

The above object can be still further achieved in the present invention by an anti-AIDS medicine comprising as an effective component a novel tripeptide compound of the following formula (III), (III)

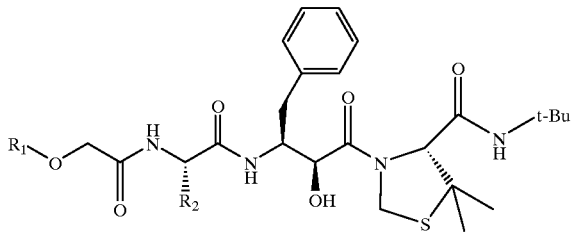

wherein $R_1$ is a phenyl group which is substituted by one amino group which is either unsubstituted or substituted by one or two (mono or di) alkyl groups each having 4 or less carbon atoms and $R_2$ represents a linear or branched alkyl group having 1–3 carbon atoms, carbamoylmethyl group, or methylthiomethyl group; or a pharmaceutically acceptable salt thereof.

BEST MODE FOR CARRYING OUT THE INVENTION

The tripeptide compound of the present invention is a hydroxymethylcarboxamide derivative containing a norstatin skeleton such as phenylalanine φ[CH(OH)C(O)N]proline or a hydroxyethylamine derivative containing a phenylalanine φ[CH(OH)CH$_2$N] decahydroisoquinolinecarboxylic acid skeleton, as a transition state mimetic structure which is essential for an HIV protease inhibition activity. Specifically, this compound has a cyclic α-amino acid which contains an amino nitrogen atom in the ring as a C-terminal amino acid in the hydroxymethylcarboxamide [CH(OH)C(O)N] moiety or a hydroxyethylamine φ[CH(OH)CH$_2$N] moiety which constitutes a transition state mimetic structure. The compound also has a tripeptide structure including an α-amino acid which is substituted by an acyl group as a protective modification group on the amino group on the N-terminal side of the dipeptide structure which constitutes the transition state mimetic structure. On the other hand, in the compounds shown by the general formula (I) or (II), the cyclic α-amino acid at the C-terminal is an α-aminocarboxamide and the nitrogen atom of carbamoyl group of this α-aminocarboxamide has a substituted or unsubstituted benzyl group. The compounds shown by the general formula (III), on the other hand, is characterized by the α-amino acid group at the N-terminal, as well as by the selection of the acyl group which is used as a protective modification group on that amino group.

First, the compound shown by the general formula (I) or (II) which is the first embodiment of the present invention will be illustrated.

The hydroxymethylcarboxamide [CH(OH)C(O)N] moiety and the hydroxyethylamine [CH(OH)CH$_2$N] moiety which constitute the transition state mimetic structure in the tripeptide compound shown by the general formula (I) of the present invention are respectively present as a 3-amino-2-hydroxy-4-substituted butanoyl skeleton [—CH$_2$CH(NH)CH(OH)C(O)—N] or a 3-amino-2- hydroxy-4-substituted butyl skeleton [—$CH_2CH(NH)CH(OH)CH_2$—N]. The steric configuration of (2S,3S) isomer is preferred for the 3-amino-2-hydroxy-4-substituted butanoyl moiety [—$CH_2CH(NH)CH(OH)C(O)$—N], whereas the steric configuration of (2R, 3S) isomer is preferred for the 3-amino-2-hydroxy-4-substituted butyl moiety [—$CH_2CH(NH)CH(OH)CH_2$—N]. On the other hand, a preferred steric configuration is (L)-isomer for the cyclic α-amino acid in which the divalent group E constitutes the ring-forming group. The steric configuration of (L)-isomer is also preferred for the α-amino acid having $R_2$ group as a side chain which forms a peptide bond at the 3 position amino group of said substituted butanoyl moiety or substituted butyl moiety.

The group which is conventionally selected for the transition state mimetic structure in a peptide compound which possesses this kind of HIV protease inhibition activity can be utilized as the group $R_3$ which is replaced on the 4 position of 3-amino-2-hydroxy-4-substitued butanoyl skeleton or 3-amino-2-hydroxy-4-substitued butyl skeleton. In the present invention, the group $R_3$ is selected from the groups which possess a substituent on an aryl group, aryloxy group or arylthio group, or on an aromatic ring included in these groups, among the groups in which the cyclic group wherein such a bonding radical is present is a 6 member cyclic group. Phenyl group, naphthyl group, phenylthio group, phenoxy group, and the like can be given as examples of $R_3$. A monocyclic or dicyclic group, particularly a monocyclic group, is preferred as the aromatic ring which constitutes this aryl group and the like. The number of substituent which is present on the aromatic ring of the group $R_3$ is preferably two or less, and more preferably one. An alkyl group having 4 or less carbon atoms, alkyloxy group, alkylamino group, halogeno group, hydroxyl group, amino group, and the like can be given as examples of the substituent. Here, the halogeno group includes chloro group, bromo group, iodine group, and fluoro group, with particularly preferred being chloro or and fluoro group.

Accordingly, among the groups possessing a substituent on aryl group, aryloxy group, or arylthio group, or on the aromatic ring group which is included in these groups, a phenyl group, phenoxy group, phenylthio group, and the like are given as preferred examples of the group $R_3$, with the phenyl group being particularly preferred.

The group which is conventionally selected for the transition state mimetic structure in a peptide compound which possesses this kind of HIV protease inhibition activity can be utilized also as the divalent group E. Specifically, this group E is a divalent hydrocarbon which may form a 5 to 7 member ring together with the adjacent nitrogen atom and carbon atom or a divalent hydrocarbon group with one or more carbon atoms in the 3–5 carbon chain of said hydrocarbon group being replaced by one or more hetero atoms, wherein said ring may form a condensed ring together with another 5 to 7 member ring or may have 3 or less substituents on that ring.

Specifically, the hetero atom which may replace for the carbon atom in the divalent group E is a nitrogen atom, sulfur atom, or oxygen atom, wherein the sulfur atom may be present as a thio group, sulfinyl group, or sulfonyl group. In the α-amino group which is formed by the group E, it is desirable that this hetero atom is bonded to neither the nitrogen atom which forms the amino group at the α-position nor the carbon atom at the α-position. In addition, the cyclic group which is formed by the group E together with the adjacent nitrogen atom and carbon atom may form a cyclic structure by condensation with another 5–7 member ring. Specifically, although the group E may be either a single ring or may form a two or more rings, when the group E is a group consisting of two or more rings formed by condensation, ortho-condensation is desirable. Alternatively, this cyclic group may possess three or less other substituents on the linear chain of this group E. The groups to be substituted here include a linear or branched aliphatic hydrocarbon group having 1–6 carbon atoms, aromatic hydrocarbon group, heteroaromatic group, hydroxyl group, a linear or branched aliphatic hydrocarbonoxy group having 1–6 carbon atoms, and halogeno group. The total number of the substituent is preferably two or less. In addition, when the number of the substituent which is replaced on the same atom in this group E is two, both of these two substituents may be members of a cyclic structure. Specifically, the two substituents may take a cross-linking structure or may be present as a dicyclic group in which the two rings combine by a spiro bond. Alternatively, the substituents may form a double bond such as an oxo group. The 5–7 member α-amino acid formed by the group E will now be illustrated more specifically by way of examples.

As examples of the α-amino acid corresponding to the 5 member cyclic group which selects the linear hydrocarbon group having three carbon atoms for this group E, proline and derivatives of proline having a substituent on the 4 position thereof, such as 4-hydroxyproline, 4-benzyloxyproline, 4-phenylproline, 4-benzylproline, 4-methylthioproline, 4-phenylthioproline, 4-fluoroproline, 4-chloroproline, and the like can be given. Given as examples of the compounds which condense by cyclization with other 5–7member cyclic groups are the compounds which cyclize with a cycloalkane, such as octahydroindole-2-carboxylic acid, octahydroiso-indole-1-carboxylic acid, 2-azabicyclo[3.3.0] octane-3-carboxylic acid; the compounds which cyclize with an aromatic group or heteroaromatic group, such as indoline-2-carboxylic acid, iso-indoline-1-carboxylic acid, and the like. As examples of the α-amino acid corresponding to the 5 member cyclic group which selects a divalent group produced by substitution of one carbon atom contained in a linear hydrocarbon group having three carbon atoms with a hetero atom as the group E, 1,3-oxazolidine-4-carboxylic acid and 1,3-thiazolidine-4-carboxylic acid, as well as 5-methyl-1,3-oxazolidine-4-carboxylic acid, 5,5-dimethyl-1,3-thiazolidine-4-carboxylic acid, and the like which possess a substituent on this 5 member heterocyclic group, can be given.

As examples of the α-amino acid corresponding to the 6 member cyclic group which selects a linear hydrocarbon group having four carbon atoms for the group E, pipecolic acid (2-piperidinecarboxylic acid) can be given. Further, given as the compounds which condense by cylization with other 5–7 member cyclic groups are decahydroisoquinoline-3-carboxylic acid and decahydroisoquinoline-1-carboxylic acid which cyclize with a cycloalkane, as well as 1,2,3,4-tetrahydro isoquinoline-3-carboxylic acid, 1,2,3,4-tetrahydro isoquinoline-1-carboxylic acid, and the like which cyclize with an aromatic group or hetero-aromatic group. Piperazine-2-carboxylic acid and the like can be given as examples of the α-amino acid corresponding to the 6 member cyclic group which selects a divalent group produced by substitution of one carbon atom contained in a linear hydrocarbon group having four carbon atoms with a hetero atom as the group E.

Among the above-described cyclic groups, 5 or 6 member monocyclic groups, particularly 5 member monocyclic groups, are preferable in the hydroxymethylcarboxamide [CH(OH)C(O)N] type compound. Specifically, as a corresponding α-amino acid, the compound shown by the following general formula (XI) is preferable.

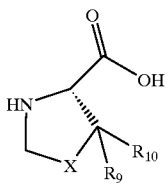

(XI)

wherein X is an oxygen atom or sulfur atom, and $R_9$ and $R_{10}$ are respectively a hydrogen atom or aliphatic hydrocarbon group having 1–6 carbon atoms. Specific examples are 1,3-oxazolidine-4-carboxylic acid and 1,3-thiazolidine-4-carboxylic acid which are the compounds having a hydrogen atom or a methyl group respectively for the groups $R_9$ and $R_{10}$ in the α-amino acid constituting this 5 member cyclic group, as well as 5-methyl-1,3-oxazolidine-4-carboxylic acid, 5,5-dimethyl-1,3-thiazolidine-4-carboxylic acid, and the like.

On the other hand, among the above-described cyclic groups, 5 or 6 member cyclic groups, particularly 6 member cyclic groups, are preferable in the hydroxyethylamine [CH(OH)CH$_2$N] type compound. Specifically, as a corresponding α-amino acid, the compound shown by the following general formula (XII) is preferable.

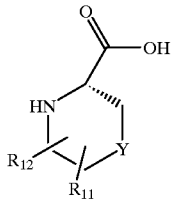

(XII)

wherein, Y is a carbon atom or nitrogen atom, and $R_{11}$ and $R_{12}$ are respectively a hydrogen atom, aliphatic hydrocarbon group which may have a branched chain, or an aromatic hydrocarbon group which may possess a substituent or a group derived from the aromatic hydrocarbon group by substitution of a hetero atom, provided that $R_{11}$ and $R_{12}$ together may form a ring.

Specifically, pipecolic acid (2-piperidinecarboxylic acid) or piperazine-2-carboxylic acid constituting a 6 member cyclic group, as well as a compound with two or less substituents which may be linear or branched aliphatic hydrocarbon groups having 1–6 carbon atoms substituting on this 6 member cyclic group or a compound condensed by cyclization with another 5–7 member cycloalkane, such as decahydroisoquinoline-3-carboxylic acid or decahydroisoquinoline-1-carboxylic acid, are preferred.

The amino acid residue having the group $R_2$ as a side chain can also be used inasmuch as the same is conventionally selected as an amino acid corresponding to the P2 position of a substrate in a transition state mimetic structure in the peptide compounds possessing this type of HIV protease inhibition activity. Therefore, the amino acid having a steric configuration corresponding to the (L)-isomer is usually desirable. Specifically, an aliphatic hydrocarbon group having 1–7 carbon atoms or an aromatic hydrocarbon group can be used for $R_2$. This aliphatic hydrocarbon group may be either linear or branched. In addition, the carbon atom constituting the bone of the aliphatic hydrocarbon group or the aromatic hydrocarbon group may be replaced by a hetero atom. Furthermore, such a carbon atom may be replaced even by a carbamoyl group, carboxyl group, or halogeno group.

The aliphatic hydrocarbon group having 1–7 carbon atoms used as $R_2$ includes linear or branched alkyl groups such as methyl group, ethyl group, propyl group, isopropyl group, butyl group, isobutyl group, sec-butyl group, tert-butyl group, as well as unsaturated hydrocarbon groups having the same carbon skeleton as these alkyl groups but including a carbon-carbon double bond, and hydrocarbon groups having a cyclic structure such as cyclohexylmethyl group, and the like. Hetero atoms which may be replaced for the skeletal carbon of these aliphatic hydrocarbon groups may be an oxygen atom, sulfur atom, nitrogen atom, and the like. Given as examples of groups replaced by an oxygen atom are those having an ether structure such as methoxymethyl group, methoxyethyl group, and the like, and those having a hydroxyl group structure such as 1-hydroxyethyl group. As examples of the groups replaced by a sulfur atom, the groups having a thioether structure such as methylthiomethyl group, methylthioethyl group, and the like are given. A group with a nitrogen atom at the terminal forming a cyano group is also included. Also included is a group with a hetero atom replacing for a carbon atom not only in the main chain, but also in a branched chain, as well as a group with a terminal carbon atom replaced by a hetero atom. In addition, groups replaced by a carbamoyl group as substituent, such as a carbamoylmethyl group, carbamoylethyl group, or by a halogeno group such as chloro group, bromo group, iodine group, fluoro group, trifluoromethoxyethyl group, trifluoromethyl group, can be given.

On the other hand, the aromatic hydrocarbon group in the group $R_2$ is the hydrocarbon group which possesses an aromatic ring, for example, an aromatic ring group such as phenyl group, or a compound having a bonding radical in a side chain hydrocarbon group which is present on the aromatic ring such as, for example, benzyl group. A nitrogen atom, oxygen atom, and sulfur atom are included in the hetero atoms which may replace for the skeletal carbon of these aromatic hydrocarbon groups. The groups having an imidazole structure, furan structure, or thiophene structure which forms a 5 member cyclic structure and exhibits aromaticity are included. As a matter of course, substitution by two or more hetero atoms is acceptable. Other substituents which may be present not only on the aromatic ring, but also in a hydrocarbon group of side chains include a carbamoyl group and a halogeno group such as chloro group, bromo group, iodine group, or fluoro group.

Any groups which have been deemed conventionally to be desirable according to the types of a dipeptide structure forming a transition state mimetic structure which combines with the C-terminal are preferably used as the group $R_2$. Specifically, preferred examples of the group $R_2$ include a methyl group, ethyl group, propyl group, isopropyl group, butyl group, isobutyl group, sec-butyl group, tert-butyl group, carbamoylmethyl group, carbamoylethyl group, methylthiomethyl group, methylthioethyl group, methoxymethyl group, methoxyethyl group, trifluoromethyl group, trifluoroethyl group, benzyl group, cyclohexylmethyl group, and the like. Particularly, in the hydroxymethylcarboxamide [CH(OH)C(O)N] type compound, Val (isopropyl group), Asn (carbamoylmethyl group), methylthioalanine (methylthiomethyl group), Ala (methyl group), 2-aminobutyric acid (ethyl group), norvaline (propyl group), norleucine (butyl group), threonine (1-hydroxyethyl group), and the like are given as preferred amino acids which have the group $R_2$ as a side chain.

In the benzyl group or substituted benzyl group which is substitued on the amide nitrogen at the C-terminal, $R_4$, $R_5$, $R_6$, $R_7$, and $R_8$ are respectively a hydrogen atom or an alkyl group having 3 or less carbon atoms, a halogeno group, amino group, hydroxyl group, aminomethyl group, hydroxymethyl group, or a mono- or di-alkyl substituted amino group replaced by an alkyl group having 3 or less carbon atoms. The halogeno group may be a chloro group, bromo group, or fluoro group, and the alkyl group having 3 or less carbon atoms may have a branched chain. Among these substituted benzyl groups, those having a substitution group at the ortho position, specifically either in the group $R_4$ or $R_8$, are particularly desirable. In addition, a small group such as a methyl group, ethyl group, halogeno group, or the like, is desirable as the group $R_4$ or $R_8$ which are replaced at the ortho position. For example, 2-methylbenzyl group, 2-chlorobenzyl group, 3-amino-2-methylbenzyl group, 5-amino-2-methylbenzyl group, 3-hydroxy-2-methylbenzyl group, 2,6-dimethylbenzyl group, 2,3-dimethylbenzyl group, 2,5-dimethylbenzyl group, and the like can be given as preferred substituted benzyl groups. More specifically, 2-methylbenzyl group and 2-chlorobenzyl group in which a methyl group or halogeno group, preferably a methyl group or chloro group, is a substitution group at the 2 position are particularly desirable as the mono-substituted benzyl group. The methyl group or halogeno group, particularly the methyl group or chloro group, is preferable also as a substitution group at the 2 position even in the multi-substituted benzyl group having substituents in addition to the 2 position.

On the other hand, the atomic group $R_1$—A—B— existing in the amino group at the N-terminal which corresponds to the P3 position in the substrate plays a role of protecting and modifying the N-terminal amino group of the tripeptide compound of the present invention. The bivalent group B forms a bond between the N-terminal amino group and the amide type. This group is either a carbonyl group (—CO—) or sulfonyl group (—SO$_2$—). The bivalent group A is an imino group (—NH—), a lower alkyl group-substituted imino group (—NR—, wherein R is an alkyl group having 6 or less carbon atoms), oxymethylene group (—O—CH$_2$—), or methyleneoxy group (—CH$_2$—O—), or a single bond. The group $R_1$ bonding to the N-terminal amino group via the group —A—B— is a hydrogen atom, an alkyl group having 6 or less carbon atoms, aromatic group or herterocyclic group having 10 or less carbon atoms. The alkyl group may have an alkyloxy group having 4 or less carbon atoms as a substituent, and the aromatic group or heterocyclic group may have a substituent selected from an alkyl group having 4 or less carbon atoms, alkyloxy group, mono or dialkyl-substituted amino group, halogeno group, hydroxyl group, amino group, or alkyl or alkenyl group having 3 or less carbon atoms substituted by a monocyclic aromatic or monocyclic heteroaromatic group. Here, the alkyl group having 6 or less carbon atoms in $R_1$ may be either linear or branched. The aromatic group or heterocyclic group having 10 or less carbon atoms in $R_1$ may be either monocyclic or dicyclic, and includes the groups having 10 or less carbon atoms which constitute this cyclic structure. The number of atoms constituting each ring is not limited to 6 inasmuch as the group has aromaticity. For example, a heterocyclic group possessing aromaticity, e.g. a group made from a 5 member ring and a 6 member ring by cyclic condensation, such as benzofuran group or benzothiophene group, is acceptable. In addition, if the number of the atom of the skeleton constituting the ring is 10 or less, the groups constituting a single conjugated system including an oxo oxygen atom of quinone such as a naphthoquinone structure, for example, are also included. Moreover, a skeleton with an atom outside the ring which forms a double bond with an atom existing on the ring and produces a skeleton with a conjugated system showing aromaticity such as, for example, a chromone moiety, is also acceptable. Inasmuch as there is at least one ring exhibiting aromaticity, the addition of a hydrogen to an unsaturated bond is allowable.

Any atomic groups $R_1$—A—B— which have been deemed conventionally preferable according to the types of the tripeptide moiety to which these groups combine, specifically according to the types of a dipeptide structure forming a transition state mimetic structure, are preferable also in the present invention. In the selection of the aromatic group or heterocyclic group having 10 or less carbon atoms replaced for the group $R_1$, among the alkyl group having 4 or less carbon atoms, alkyloxy group, and mono- or di-alkyl-substituted amino group, the alkyl group may be either linear or branched and the halogeno group means chloro group, bromo group, or fluoro group. In addition, the alkyl or alkenyl group having 3 or less carbon atoms substituted by a monocyclic aromatic or monocyclic heteroaromatic group which can be present as a substitution group on the aromatic group or heterocyclic group having 10 or less carbon atoms includes an alkyl or alkenyl group having 3 or less carbon atoms substituted by a monocyclic aromatic ring group, specifically, by a phenyl group having a side chain, such as a phenyl group, tolyl group, xylyl group, or mesityl group, or an alkyl or alkenyl group having 3 or less carbon atoms substituted by a monocyclic heteroaromatic group, for example, a 5 member group such as a furyl group or 6 member group such as a pyridyl group. Specifically, these are benzyl group, phenethyl group, cinnamyl group, or the like. When an alkyl or alkenyl group having 3 or less carbon atoms substituted by a monocyclic heteroaromatic group is included as a substitution group, it is preferable that the aromatic or heteroaromatic ring which is a moiety of the group $R_1$ be a monocyclic group and the atomic group $R_1$—A—B— should not be a large group. Therefore, when an alkyl or alkenyl group having 3 or less carbon atoms substituted by a monocyclic aromatic group or a monocyclic heteroaromatic group is included as a substitution group, the number of this group is preferably one.

In addition, when an alkyl group having 6 or less carbon atoms with or without a substitution group is selected for $R_1$ in the atomic group $R_1$—A—B—, the atomic group $R_1$—A—B— as a whole is preferably an acyl group with a chain structure, such as an alkoxylacetyl group wherein A is an oxymethylene group (—O—CH$_2$—) and B is a carbonyl group (—CO—), an alkoxylcarbonyl group wherein A is a methyleneoxy group (—CH$_2$—O—) and B is a carbonyl group (—CO—), an alkanoyl group wherein A is a single bond and B is a carbonyl group (—CO—), or an alkoxyalkoxylcarbonyl group which is a group with an alkyloxy group having 4 or less carbon atoms substituted on the group $R_1$ of these groups. The chain structure may be branched, but the number of the branch is preferably one.

In addition, in the atomic group $R_1$—A—B—, the group wherein B is a carbonyl group (—CO—) is more preferable than the group wherein B is a sulfonyl group (—SO$_2$—).

Selecting a combination of the groups which are mentioned as desirable groups in the above description will make an ideal compound. The tripeptide compound shown by the following general formula (II) can be given as still another preferred embodiment of the hydroxymethylcarboxamide [CH(OH)C(O)N] type compound:

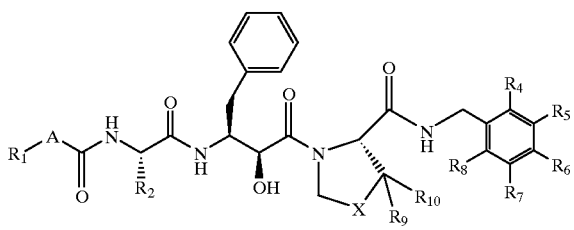

(II)

wherein A, $R_1$, $R_2$, $R_4$, $R_5$, $R_6$, $R_7$, and $R_8$ are the same as defined in the above general formula (I), X denotes an oxygen atom or sulfur atom; and $R_9$ and $R_{10}$ respectively represent a hydrogen atom or a linear or branched aliphatic hydrocarbon group having 1–6 carbon atoms.

The compound with a sulfur atom for X in the general formula (II) is a particularly desirable compound.

Further, the tripeptide compound shown by the following general formula (IV) can be given as still another preferred embodiment of the hydroxyethylamine [CH(OH)CH$_2$N] type compound,

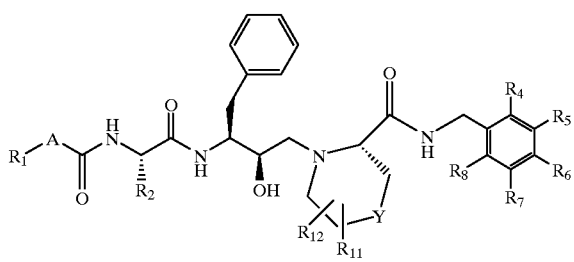

(IV)

wherein A, $R_1$, $R_2$, $R_4$, $R_5$, $R_6$, $R_7$, and $R_8$ are the same as defined in the general formula (I), Y is a carbon atom or nitrogen atom, and $R_{11}$ and $R_{12}$ are respectively a hydrogen atom, a linear or branched aliphatic hydrocarbon group, an aromatic hydrocarbon group which may have a substituent, or a group derived from such an aromatic group by substitution of a hetero atom, provided that $R_{11}$ and $R_{12}$ may form a bond together.

Among the compounds of the general formula (II), the tripeptide compound containing a sulfur atom as the group X in the 5 member cyclic a-amino acid, specifically, the compound shown by the following general formula (V), can be given as one preferred embodiment:

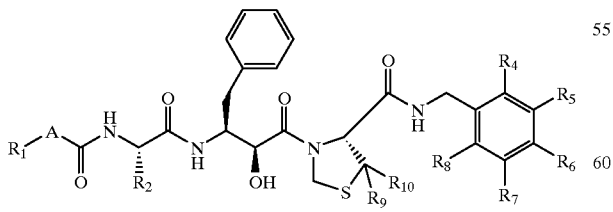

(V)

wherein A, $R_1$, $R_2$, $R_4$, $R_5$, $R_6$, $R_7$, and $R_8$ are the same as defined in the above general formula (I) and $R_9$ and $R_{10}$ are respectively a hydrogen atom or a linear or branched aliphatic hydrocarbon group having 1–6 carbon atoms.

As an example of the compound which is represented by the above general formula (II), (4S,5R)-N-(2-methylbenzyl)-3-{(2S,3S)-2-hydroxy-3-[N-(benzyloxycarbonyl)-L-asparaginyl]amino-4-phenylbutanoyl}-5-methyl-1,3-oxazolidine-4-carboxamide (Z-Asn-Apns-Mox-NHBzl(2-Me)) can be given.

Specific examples of the compound which is represented by the general formula (V) include:
(R)-N-(2-methylbenzyl)-3-{(2S,3S)-2-hydroxy-3-[N-(benzyloxycarbonyl)-L-asparaginyl]amino-4-phenylbutanoyl}-1,3-thiazolidine-4-carboxamide (Z-Asn-Apns-Mox-NHBzl(2-Me)),
(R)-N-(2-methylbenzyl)-3-{(2S,3S)-2-hydroxy-3-[N-(2-chromonecarbonyl)-L-asparaginyl]amino-4-phenylbutanoyl}-1,3-thiazolidine-4-carboxamide (Chc-Asn-Apns-Thz-NHBzl(2-Me)),
(R)-N-benzyl-3-{(2S,3S)-2-hydroxy-3-N-(benzyloxycarbonyl)-L-asparaginyl]amino-4-phenylbutanoyl}-5,5-dimethyl-1,3-thiazolidine-4-carboxamide (Z-Asn-Apns-Dmt-NHBzl),
(R)-N-(3-amino-2-methylbenzyl)-3-{(2S,3S)-2-hydroxy-3-[N-(benzyloxycarbonyl)-L-asparaginyl]amino-4-phenylbutanoyl}-5,5-dimethyl-1,3-thiazolidine-4-carboxamide (Z-Asn-Apns-Dmt-NHBzl(3-NH$_2$,2-Me)),
(R)-N-(3-aminobenzyl)-3-{(2S,3S)-2-hydroxy-3-[N-(benzyloxycarbonyl)-L-asparaginy]amino-4-phenylbutanoyl}-5,5-dimethyl-1,3-thiazolidine-4-carboxamide (Z-Asn-Apns-Dmt-NHBzl(3-NH$_2$)), and
(R)-N-(3-hydroxy-2-methylbenzyl)-3-{(2S,3S)-2-hydroxy-3-[N-(benzyloxycarbonyl)-L-asparaginyl]amino-4-phenylbutanoyl}-5,5-dimethyl-1,3-thiazolidine-4-carboxamide (Z-Asn-Apns-Dmt-NHBzl(3-OH,2-Me)).

In addition, tripeptide compounds represented by the following general formula (VI), (VII), and (VIII):

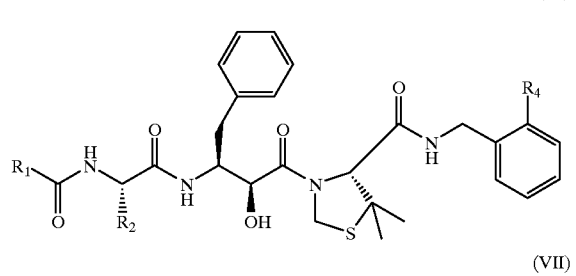

(VI)

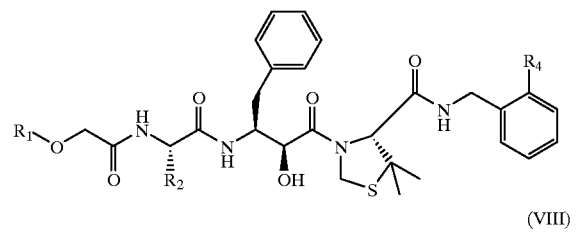

(VII)

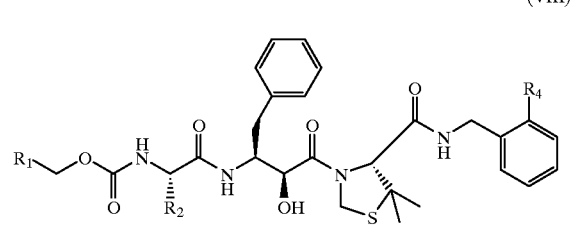

(VIII)

wherein $R_1$ is the same as defined in the general formula (I), $R_2$ is a methyl group, ethyl group, propyl group, isopropyl group, carbamoylmethyl group, or methylthiomethyl group, and $R_4$ is a methyl group or a chloro group, are given as particularly preferred embodiments of the compounds having the above-described general formula (V).

Particularly preferred compounds represented by the general formula (VI), (VII) or (VIII) are those having a phenyl group, 2-chromone group, benzofuran-2-yl group, 5-isoquinolyl group, benzothiazol-2-yl group, 2-quinolyl group, benzimidazol-2-yl group, or the like for the group $R_1$. Specific examples include:

(R)-N-(2-methylbenzyl)-3-{(2S,3S)-2-hydroxy-3-[N-(benzyloxycarbonyl)-L-asparaginyl]amino-4-phenylbutanoyl}-5,5-dimethyl-1,3-thiazolidine-4-carboxamide (Z-Asn-Apns-Dmt-NHBzl(2-Me)), (R)-N-(2-chlorobenzyl)-3-{(2S,3S)-2-hydroxy-3-[N-(benzyloxycarbonyl)-L-asparaginyl]amino-4-phenylbutanoyl}-5,5-dimethyl-1,3-thiazolidine-4-carboxamide (Z-Asn-Apns-Dmt-NHBzl(2-Cl)), (R)-N-(2-methylbenzyl)-3-{(2S,3S)-2-hydroxy-3-[N-(benzyloxycarbonyl)-L-valyl]amino-4-phenylbutanoyl}-5,5-dimethyl-1,3-thiazolidine-4-carboxamide (Z-Val-Apns-Dmt-NHBzl(2-Me))

(R)-N-(2-methylbenzyl)-3-{(2S,3S)-2-hydroxy-3-[N-(2-chromonecarbonyl)-L-asparaginyl]amino-4-phenylbutanoyl}-5,5-dimethyl-1,3-thiazolidine-4-carboxamide (Chc-Apns-Dmt-NHBzl(2-Me)), (R)-N-(2-methylbenzyl)-3-{(2S,3S)-2-hydroxy-3-[N-(benzofuran-2-ylcarbonyl)-L-asparaginyl]amino-4-phenylbutanoyl}-5,5-dimethyl-1,3-thiazolidine-4-carboxamide (Bfc-Apns-Dmt-NHBzl(2-Me)), (R)-N-(2-methylbenzyl)-3-{(2S,3S)-2-hydroxy-3-[N-(5-isoquinclyloxyacetyl)-L-valyl]amino-4-phenylbutanoyl}-5,5-dimethyl-1,3-thiazolidine-4-carboxamide (iQoa-Val-Apns-Dmt-NHBzl(2-Me)), (R)-N-(2-methylbenzyl)-3-{(2S,3S)-3-[N-(2-benzofurancarbonyl)-L-valyl]amino-2-hydroxy-4-phenylbutanoyl}-5,5-dimethyl-1,3-thiazolidine-4-carboxamide (Bfc-Val-Apns-Dmt-NHBzl(2-Me)), (R)-N-(2-methylbenzyl)-3-{(2S,3S)-3-[N-(2-chromonecarbonyl)-L-valyl]amino-2-hydroxy-4-phenylbutanoyl}-5,5-dimethyl-1,3-thiazolidine-4-carboxamide (Chc-Val-Apns-Dmt-NHBzl(2-Me)), (R)-N-(2-methylbenzyl)-3-{(2S,3S)-3-[N-(2-quinolinecarbonyl)-L-valyl]amino-2-hydroxy-4-phenylbutanoyl}-5,5-dimethyl-1,3-thiazolidine-4-carboxamide (2-Quic-Val-Apns-Dmt-NHBzl(2-Me)), (R)-N-(2-methylbenzyl)-3-{(2S,3S)-3-[N-(2-benzothiazolecarbonyl)-L-valyl]amino-2-hydroxy-4-phenylbutanoyl}-5,5-dimethyl-1,3-thiazolidine-4-carboxamide (Btc-Val-Apns-Dmt-NHBzl(2-Me)), (R)-N-(2-methylbenzyl)-3-{(2S,3S)-3-N-(2-benzimidazolecarbonyl)-L-valyl]amino-2-hydroxy-4-phenylbutanoyl}-5,5-dimethyl-1,3-thiazolidine-4-carboxamide (Bic-Val-Apns-Dmt-NHBzl(2-Me)), (R)-N-(2-methylbenzyl)-3-{(2S,3S)-3-[N-(7-methoxybenzofuran-2-carbonyl)-L-valyl]amino-2-hydroxy-4-phenylbutanoyl}-5,5-dimethyl-1,3-thiazolidine-4-carboxamide ((7-MeO)Bfc-Val-Apns-Dmt-NHBzl(2-Me)), (R)-N-(2-methylbenzyl)-3-{(2S,3S)-3-[N-(3-benzylphenoxyacetyl)-L-asparaginyl]amino-2-hydroxy-4-phenylbutanoyl}-5,5-dimethyl-1,3-thiazolidine-4-carboxamide ((3-Bzl)Phoa-Asn-Apns-Dmt-NHBzl(2-Me)), (R)-N-(2-methylbenzyl)-3-{(2S,3S)-3-[N-(2-quinoxalinecarbonyl)-L-asparaginyl]amino-2-hydroxy-4-phenylbutanoyl}-5,5-dimethyl-1,3-thiazolidine-4-carboxamide (2-Qxc-Asn-Apns-Dmt-NHBzl(2-Me)), (R)-N-(2-methylbenzyl)-3-{(2S,3S)-3-[N-(2-quinoxalinecarbonyl)-L-valyl]amino-2-hydroxy-4-phenylbutanoyl}-5,5-dimethyl-1,3-thiazolidine-4-carboxamide (2-Qxc-Val-Apns-Dmt-NHBzl(2-Me)), (R)-N-(2-methylbenzyl)-3-{(2S,3S)-2-hydroxy-3-[(S)-2-(7-methoxy-2-benzofurancarbonyl)aminopropanoyl]amino-4-phenylbutanoyl}-5,5-dimethyl-1,3-thiazolidine-4-carboxamide ((7-MeO) Bfc-Ala-Apns-Dmt-NHBzl(2-Me)), (R)-N-(2-methylbenzyl)-3-{(2S,3S)-2-hydroxy-3-[(S)-2-(3-quinolinecarbonyl)amino-3-methylbutanoyl]amino-4-phenylbutanoyl}-5,5-dimethyl-1,3-thiazolidine-4-carboxamide (3-Quic-Val-Apns-Dmt-NHBzl(2-Me)), (R)-N-(2-methylbenzyl)-3-{(2S,3S)-2-hydroxy-3-[(S)-2-(3-dimethylaminophenoxyacetyl)amino-3-methylbutanoyl]amino-4-phenylbutanoyl}-5,5-dimethyl-1,3-thiazolidine-4-carboxamide ((3- $Me_2N$) Phoa-Val-Apns-Dmt-NHBzl(2-Me)), (R)-N-(2-methylbenzyl)-3-{(2S,3S)-2-hydroxy-3-[(S)-2-(5-quinolinyloxyacetyl)amino-3-methylbutanoyl]amino-4-phenylbutanoyl}-5,5-dimethyl-1,3-thiazolidine-4-carboxamide (5-Qoa-Val-Apns-Dmt-NHBzl(2-Me)), (R)-N-(2-methylbenzyl)-3-{(2S,3S)-2-hydroxy-3-[(S)-2-(6-quinolinyloxyacetyl)aminobutanoyl]amino-4-phenylbutanoyl}-5,5-dimethyl-1,3-thiazolidine-4-carboxamide (6-Qoa-Abu-Apns-Dmt-NHBzl(2-Me)), (R)-N-(2-methylbenzyl)-3-{(2S,3S)-2-hydroxy-3-[(S)-2-(3-dimethylaminophenoxyacetyl)aminobutanoyl]amino-4-phenyl butanoyl}-5-5-dimethyl-1,3-thiazolidine-4-carboxamide((3-$Me_2N$)Phoa-Abu-Apns-Dmt-NHBzl(2-Me)), and (R)-N-(2-methylbenzyl)-3-{(2S,3S)-2-hydroxy-3-[(S)-2-(3-dimethylaminophenoxyacetyl)aminopropanoyl]amino-4-phenylbutanoyl}-5,5-dimethyl-1,3-thiazolidine-4-carboxamide ((3-$Me_2N$) Phoa-Ala-Apns-Dmt-NHBzl(2-Me))

Other preferred compounds are those having a hydrogen, methyl group, ethyl group, methoxymethyl group, ethoxymethyl group, or the like for $R_1$ in the formula (VI), (VII), or (VIII). Specific examples include:

(R)-N-(2-methylbenzyl)-3-{(2S,3S)-2-hydroxy-3-[(S)-2-(methoxycarbonyl)amino-3-methylbutanoyl]amino-4-phenylbutanoyl}l-5,5-dimethyl-1,3-thiazolidine-4-carboxamide (MeO-CO-Val-Apns-Dmt-NHBzl-(2-Me)), (R)-N-(2-methylbenzyl)-3-{(2S,3S)-2-hydroxy-3-[(S)-2-(methoxycarbonyl)aminobutanoyl]amino-4-phenylbutanoyl}-5,5-dimethyl-1,3-thiazolidine-4-carboxamide (MeO-CO-Abu-Apns-Dmt-NHBzl(2-Me)), (R)-N-(2-methylbenzyl)-3-{(2S,3S)-2-hydroxy-3-[(S)-2-(ethoxycarbonyl)amino-3-methylbutanoyl]amino-4-phenylbutanoyl}-5,5-dimethyl-1,3-thiazolidine-4-carboxamide (EtO-CO-Val-Apns-Dmt-NHBzl(2-Me)), (R)-N-(2-methylbenzyl)-3-{(2S,3S)-2-hydroxy-3-[(S)-2-(methoxyethoxycarbonyl)amino-3-methylbutanoyl]amino-4-phenylbutanoyl}-5,5-dimethyl-1,3-thiazolidine-4-carboxamide (MeO-$(CH_2)_2$-O-CO-Val-Apns-Dmt-NHBzl(2-Me)), (R)-N-(2-methylbenzyl)-3-{(2S,3S)-2-hydroxy-3-[(S)-2-(methoxyacetyl)amino-3-methylbutanoyl]amino-4-phenylbutanoyl}-5,5-dimethyl-1,3-thiazolidine-4-carboxamide (MeO-$CH_2$-CO-Val-Apns-Dmt-NHBzl(2-Me))

(R)-N-(2-methylbenzyl)-3-{(2S,3S)-2-hydroxy-3-[(S)-2-(ethoxyacetyl)amino-3-methylbutanoyl]amino-4-phenylbutanoyl}-5,5-dimethyl-1,3-thiazolidine-4-carboxamide (EtO-$CH_2$-CO-Val-Apns-Dmt-NHBzl(2-Me)), (R)-N-(2-methylbenzyl)-3-{(2S,3S)-2-hydroxy-3-[(S)-2-acetylamino-3-methylbutanoyl]amino-4-phenylbutanoyl}-5,5-dimethyl-1,3-thiazolidine-4-carboxamide (Ac-Val-Apns-Dmt-NHBzl(2-Me)), (R)-N-(2-methylbenzyl)-3-{(2S,3S)-2-hydroxy-3-[(S)-2-acetylaminobutanoyl]amino-4-phenylbutanoyl}-5-5-dimethyl-1,3-thiazolidine-4-carboxamide (Ac-Abu-Apns-Dmt-NHBzl(2-Me)), (R)-N-(2-methylbenzyl)-3-{(2S,3S)-2-hydroxy-3-[N-(methoxycarbonyl)-L-threonyl]amino-4-phenylbutanoyl}-5,5-dimethyl-1,3-thiazolidine-4-carboxamide (MeO-CO-Thr-Apns-Dmt-NHBzl(2-Me)), (R)-N-(2-methylbenzyl)-3-{(2S,3S)-2-hydroxy-3-[N-(methoxycarbonyl)-L-asparaginyl]amino-4-phenylbutanoyl}-5-5-dimethyl-1,3-thiazolidine-4-carboxamide (MeO-CO-Asn-Apns-Dmt-NHBzl(2-Me)).

Next, the compound represented by the general formula (III) which is another embodiment of the present invention will be explained.

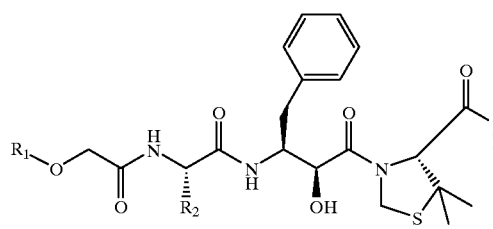

(III)

wherein $R_1$ and $R_2$ are the same as defined above.

The compound represented by the general formula (III) possesses a form similar to the compound represented by the above general formula (VII) except that a substituent on the C-terminal amide nitrogen atom is a tert-butyl group instead of a substituted benzyl group. Specifically, $R_2$ is selected from a methyl group, ethyl group, propyl group, isopropyl group, carbamoylmethyl group, or methylthiomethyl group as well as $R_2$ in the above-mentioned general formula (VII). Preferably, $R_2$ is selected from an ethyl group, propyl group, isopropyl group, carbamoylmethyl group, and methylthiomethyl group. One feature characterizing the compound represented by the general formula (III) is that a substituted phenoxyacetyl group exists on the N-terminal amino group of a-amino acid residue having the group $R_2$ as the side chain as a protective modification group. As the substituted phenoxyacetyl group which is $R_1$, mono-substituted phenyl group which is substituted by an amino group or mono- or di-alkyl substituted amino group having 4 or less carbon atoms, and preferably mono-substituted phenyl group in which mono- or di-alkyl substituted amino group substitutes on the 3 position thereof is selected. As particularly preferred examples of the compound, the following compounds in which a phenyl group is selected as $R_1$, wherein a methylamino group or a dimethylamino group substitutes on the 3 position thereof, can be given:

(R)-N-tert-butyl-3-{(2S,3S)-2-hydroxy-3-[(S)-2-(3-dimethylaminophenoxyacetyl)amino-3-methylbutanoyl]amino-4-phenylbutanoyl}-5,5-dimethyl-1,3-thiazolidine-4-carboxamide ((3-Me$_2$N) Phoa-Val-Apns-Dmt-NHtBu) and (R)-N-tert-butyl-3-{(2S,3S)-2-hydroxy-3-[(S)-2-(3-dimethylaminophenoxyacetyl)aminobutanoyl]amino-4-phenylbutanoyl}-5,5-dimethyl-1,3-thiazolidine-4-carboxamide ((3-Me$_2$N) Phoa-Abu-Apns-Dmt-NHtBu).

The pharmaceutically acceptable salt of the tripeptide compound of the present invention includes a substituent which substitutes on a substituted benzyl group or a cyclic group of $R_1$, which exists in the compound, or, for example, in the case where a basic nitrogen atom is present in the other condensed rings, a salt which is formed from the nitrogen atom and various pharmaceutically acceptable acid, and specifically, a pharmaceutically acceptable salt such as a hydrogen chloride, acetic acid salt, or methanesulfonate. Pharmaceutically acceptable salts formed from a phenolic hydroxyl group which substitutes on a substituted benzyl group and the like and various pharmaceutically acceptable mono-valent cations are also given as examples. A typical example of such a pharmaceutically acceptable salt is a sodium salt.

The tripeptide compounds of the present invention represented by the general formula (I) are composed of (i) a tripeptide skeleton which is indispensable for the HIV protease inhibition activity and consists of a dipeptide moiety in which the substituted benzyl group substitutes on a nitrogen atom of amide at the C-terminal and an a-amino acid residue which is present at the N-terminal, and (ii) an atomic group which protectively substitutes the N-terminal α-amino group of the tripeptide skeleton. For example, an intermediate material compound represented by the following general formula (XIII),

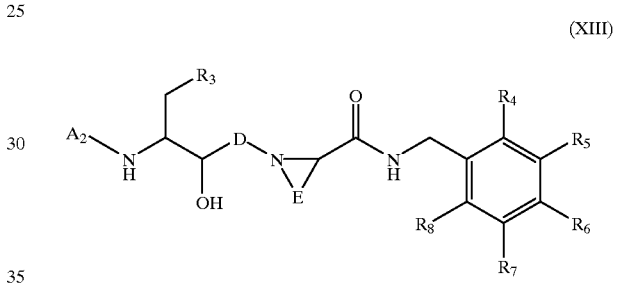

(XIII)

wherein D, E, $R_3$, $R_4$, $R_5$, $R_6$, $R_7$, and $R_8$ are the same as defined in the general formula (I) and $A_2$ is a protective group commonly used with an amino group, which forms the dipeptide moiety is previously prepared according to the following processes by a conventionally known method. After release of the protective group $A_2$ by an acid treatment, the tripeptide skeleton represented by the following general formula (XIV) is obtained by an elongation of the α-amino acid residue of which $R_2$ is the side chain to the N-terminal amino group of the intermediate material.

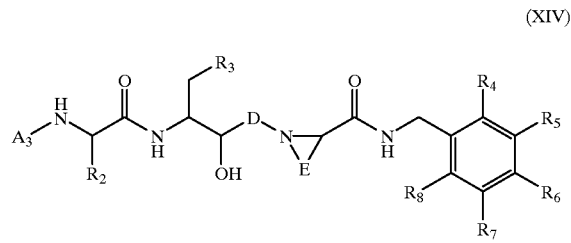

(XIV)

wherein D, E, $R_2$, $R_3$, $R_4$, $R_5$, $R_6$, R7, and $R_8$ are the same as defined in the general formula (I) and $A_3$ is a protective group commonly used with an amino group.

Finally, the atomic group $R_1$—A—B is introduced into the N-terminal amino group of the tripeptide skeleton by an N-acylation and the like, whereby the intermediate material compound can be prepared. As the commonly used protective group for the amino groups represented by $A_2$ and $A_3$, a protective group which is easily released by an acid treatment is used. Process for preparing the hydroxyethylamine derivatives and hydroxymethylcarboxamide derivatives will be described in more detail.

[1] Process for preparing hydroxyethylamine type derivatives

A process for preparing the hydroxyethylamine type derivatives of the present invention, namely, the compound which is represented by the following general formula (IX),

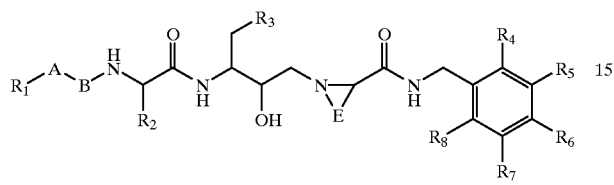

(IX)

wherein $R_1, A_2, B, E, R_3, R_4, R_5, R_6, R_7$, and $R_8$ are the same as defined in the general formula (I), will now be summarized.

Step 1-1
Preparation of Intermediate Material Compound Represented by the General Formula (XIII)

This compound corresponds to an intermediate material in a synthetic method of a hydroxyethylamine type HIV protease inhibitor, of which the preparation method has reported in various publications (see, for example, Science 248, 358-361 (1990), N. A. Roberts et al., B. M. Kim et al., Bioorg. & Med. Chem. Lett. 4, 2273-2278 (1994)). For example, a cyclic α-amino acid derivative with a protected N-terminal represented by the general formula (XV),

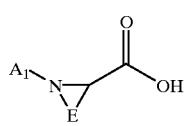

(XV)

wherein $R_1, A_2, B, E, R_3, R_4, R_5, R_6, R_7$, and $R_8$ are the same as defined in the general formula (I), will now be summarized.
wherein E is the same as defined in the general formula (I) and $A_1$ is a commonly used protective group for an amino group, and a substituted benzylamine represented by the following general formula (XVI),

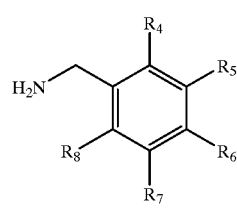

(XVI)

wherein E, $R_4$, $R_5$, $R_6$, $R_7$, and $R_8$ are the same as defined in the general formula (I), are reacted according to a conventional method to prepare an amide bond, thereby obtaining a cyclic α-aminocarboxamide derivative with protected N-terminal which is represented by the following general formula (XVII),

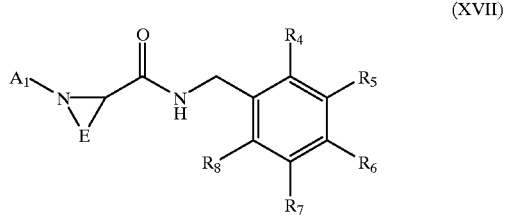

(XVII)

wherein E, $R_4$, $R_5$, $R_6$, $R_7$, and $R_8$ are the same as defined in the general formula (I) and $A_1$ is a commonly used protective group for an amino group of the general formula (XV).

After release of the N-terminal protective group $A_1$ of the cyclic α-amino-carboxamide derivative, the resulting compound is reacted with an N-terminal protected aminoepoxide derivative represented by the following general formula (XVIII),

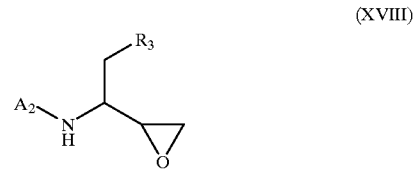

(XVIII)

wherein $R_3$ is the same as defined in the general formula (I) and $A_2$ is a commonly used protective group for an amino group, in a solvent such as iso-propanol while heating under refluxing to ring-open the epoxide with the amine, thereby obtaining an amino alcohol derivative represented by the following general formula (XIX),

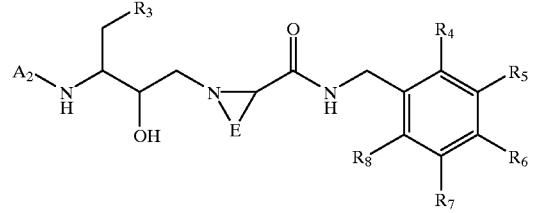

(XIX)

wherein E, $R_3$, $R_4$, $R_5$, $R_6$, $R_7$, and $R_8$ are the same as defined in the general formula (I) and $A_2$ is a commonly used protective group for an amino group of said general formula (XVIII). After release of the N-terminal protective group $A_2$ of the amino alcohol derivative, a dipeptide intermediate material represented by the following general formula (XX) in which a methylene group is selected as the group D in the general formula (XIII) can be obtained.

(XX)

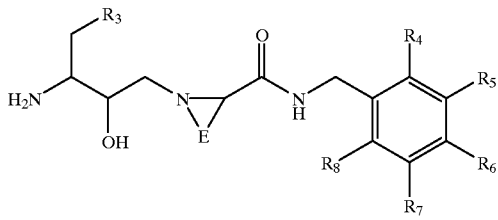

wherein E, $R_3$, $R_4$, $R_5$, $R_6$, $R_7$, and $R_8$ are the same as defined in the above-mentioned general formula (I).

In this ring-opening reaction of the epoxy ring, if (2R,3S)-derivative is used for a steric configuration of the aminoepoxide derivative, the steric configuration of the resulting dipeptide intermediate material is also the (2R,3S)-type. Thus, an optical isomer having the same steric configuration as the raw material can be obtained.

Step 1–2

Elongation of Peptide Chain

An N-terminal protected α-amino acid represented by the following general formula (XXI), (XXI)

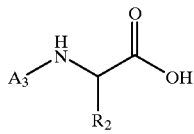

wherein $R_2$ is the same as defined in the general formula (I) and $A_3$ is a commonly used protective group for an amino group in the general formula (XIV), and a carbodiimide such as DCC (N,N'-dicyclohexylcarbodiimide) or an acid anhydride such as an acetic anhydride or trifluoroacetic anhydride to prepare the α-amino acid anhydride, active ester, or the like which is represented by the following general formula (XXII), (XXII)

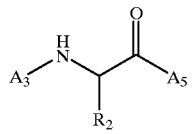

wherein $R_2$ is the same as defined in the general formula (I), $A_3$ is a commonly used protective group for an amino group of the general formula (XXI), and $A_5$ is a leaving group. Here, the atomic group represented by $A_5$ is derived from a reagent for synthesizing the peptide. This α-amino acid anhydride, active ester derivative, or the like which is represented by the general formula (XXII) is reacted with the intermediate material which is represented by the general formula (XX) in a solvent such as N,N-dimethylformamide (DMF) to obtain a tripeptide skeleton represented by the following general formula (XXIII), (XXIII)

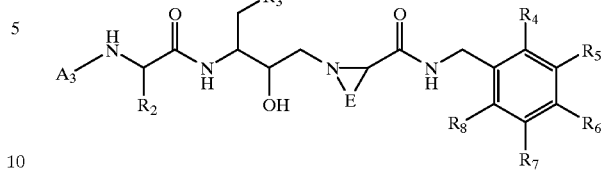

wherein E, $R_2$, $R_3$, $R_4$, $R_5$, $R_6$, $R_7$, and $R_8$ are the same as defined in the general formula (I) and $A_3$ is a commonly used protective group for an amino group of the general formula (XXI).

Step 1–3

N-acylation

If the atomic group $R_1$—A—B— is an acyl group type, the atomic group $R_1$—A—B— can be introduced by the following N-acylation, for example.

A carboxylic acid represented by the following general formula (XXIV), $$R_1-A-COOH \qquad (XXIV)$$

wherein $R_1$ and A are the same as defined in the general formula (I), is reacted with a carbodiimide such as DCC (N,N'-dicyclohexylcarbodiimide) and an acid anhydride such as an acetic anhydride or trifluoroacetic anhydride to prepare an acid anhydride of the carboxylic acid or the like represented by the following general formula (XXV), (XXV)

wherein $R_1$ and A are the same as defined in the general formula (I) and $A_5$ is a leaving group.

Then, the acid anhydride of the carboxylic acid represented by the general formula (XXV) is reacted with the above-described intermediate material with the group $A_3$ removed represented by the general formula (XXIII) in which a methylene group is selected as the group D in a solvent such as N,N-dimethylformamide (DMF) to obtain the target N-acylated hydroxyethylamine type derivative represented by the general formula (IX).

The atomic group $R_1$—A—B— of which the group B is a sulfonyl group which becomes a sulfonamide by forming a bond with the N-terminal amino group can be introduced by a similar method to the above-mentioned N-acylation such as a method using a sulfonyl chloride or a method using a sulfonic acid anhydride and active ester derivative. If —A—B— of the atomic group $R_1$—A—B— is —NH—CO— which becomes a ureylene configuration by forming a bond with the N-terminal amino group, the target compound can be prepared by a condensation with the N-terminal amino group using an isocyanate $R_1$—N=C=O.

In the case where a substituent which may cause an undesirable side-reaction in the course of the above reaction is present in addition to the reaction groups, such a substituent should be appropriately protected by a protective group at the time of reaction and the following reactions should be performed after release of the substituent. The amino group which substitutes on a substituted benzyl group or the like can be reacted as a nitro group, then converted into the amino group by reduction.

[2] Process for Preparing Hydroxymethylcarboxamide Type Derivative

A process for preparing the hydroxymethylcarboxamide type derivative of the present invention, specifically, the compound which is represented by the following general formula (X),

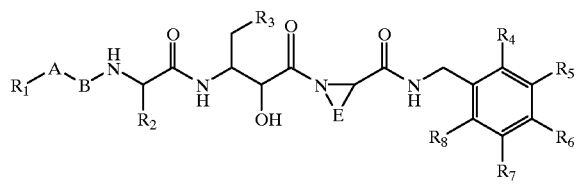

(X)

wherein $R_1$, A, B, E, $R_2$, $R_3$, $R_4$, $R_5$, $R_6$, $R_7$, and $R_8$ are the same as defined in the general formula (I) will be described.

Step 2–1
Preparation of Intermediate Material Compound Represented by the General Formula (XIII)

The intermediate material compound corresponds to an intermediate material in a synthetic method of a hydroxymethylcarboxamide type HIV protease inhibitor and the preparation method has been reported in various publications (see, for example, Yoshiaki Kiso, Journal of Synthetic Organic Chemistry Japan vol. 52, 403–412 (1994)). For example, an α-amino-carboxamide derivative represented by the general formula (XVII) is subjected to a condensation with an N-protected derivative of 3-amino-2-hydroxy-4-substituted butanoic acid represented by the following general formula (XXVI),

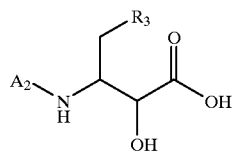

(XXVI)

wherein $R_3$ is the same as defined in the general formula (I) and $A_2$ is a common protective group for an amino group releasable with an acid, using a carbodiimide such as DCC or EDC and an additive compound such as HONB (N-hydroxy-norbornene-2,3-dicarboxyimide) or HOBt (N-hydroxybenzotriaole) to form a peptide bond, thereby obtaining an N-protected dipeptide derivative represented by the following general formula (XXVII),

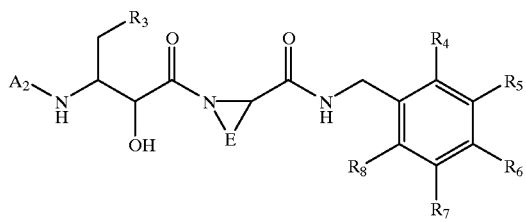

(XXVII)

wherein E, $R_3$, $R_4$, $R_5$, $R_6$, $R_7$, and $R_8$ are the same as defined in the general formula (I) and $A_2$ is the same group as the common protective group for an amino group of the general formula (XXVI).

Secondly, after release of the N-terminal protective group of the N-protected dipeptide derivative using an acid such as hydrogen chloride in dioxane, an intermediate material represented by the general formula (XIII) from which $A_2$ has been removed and a carbonyl group is selected as the group D can be obtained. If the (2S-3S)-derivative, for example, is used for a steric configuration of the 3-amino-2-hydroxy-4-substituted butanoic acid N-protected derivative, the steric configuration of the resulting dipeptide intermediate material is also the (2S-3S)-type. Thus, an optical isomer having the same steric configuration as the raw material can be obtained.

Step 2–2
Elongation of Peptide Chain

Step 2–3
N-acylation According to the above peptide chain-elongation step 1–2 and the N-acylation step 1–3, the target hydroxymethylcarboxamide type derivative represented by the general formula (X) can be obtained by reacting the intermediate material represented by the general formula (XIII) prepared in the step 2–1 in which a carbonyl group is selected as the group D, with an amino acid represented by the general formula (XXII), then with a carboxylic acid represented by the general formula (XXIV).

The hydroxyethylamine type derivative represented by the general formula (IX) or the hydroxymethylcarboxamide type derivative represented by the general formula (X) which are prepared by the above process can be used as the HIV protease inhibitor by removing impurities using a purification method such as recrystallization as required. In addition, since the tripeptide compound of the present invention is prepared from the intermediate material represented by the general formula (XIII), an amino acid represented by the general formula (XXII), a carboxylic acid represented by the general formula (XXIV), and the like as raw materials, the molecular structure can be easily identified by means of a spectroscopy technique such as a nuclear magnetic resonance method or an infrared absorption method with reference to each configuration respectively originated from these compounds. On the other hand, since the tripeptide compound of the present invention which is represented by the general formula (III) is the same as the compound represented by the above general formula (VII) except that the C-terminal substituted benzyl group is replaced by a tert-butyl group, the synthesis itself can be carried out by a completely similar process. Specifically, almost the same synthetic conditions can be employed except for the use of a tert-butylamine instead of a substituted benzylamine which is one of the starting materials so that the synthesis can be easily carried out.

The tripeptide compound of the present invention can be administered as a medicine using a commonly used carrier for medicine or an excipient according to a conventional method when clinically applied as an anti-AIDS medicine. The tripeptide compound of the present invention can be used in the form of, for example, an injection agent such as a muscle injection agent or an intravenous injection agent, a parenteral administration agent such as a spray agent or a suppository, or an oral administration agent such as a granulars, capsules, or tablets. The medicine is administered at a dose in the range of usually 0.5–50 mg/kg, and preferably 3–30 mg/kg, for an adult 2 to 4 times a day, although a specific dose is appropriately determined according to the symptom of the subject, the purpose of treatment such as controlling AIDS symptoms from exhibiting or progressing, the age and sex of the subject. In addition, when the tripeptide compound is used as a peroral drug, a dosage form applied to oral administration of various synthetic peptide compounds which have already been proposed as the HIV protease inhibitor can be employed (see, for example, Japanese Patent Application Laid-open No. 208478/1996).

The dipeptide compound of the present invention and the process for preparing the compound will now be described in detail by way of examples. Also described are examples showing the characteristics of the tripeptide compound of the present invention such as superior anti-HIV activity due to the high HIV protease inhibition action and low cytotoxic properties which make this compound suitable as a medicine. These examples should by no means be construed as limiting the present invention.

Apns ((2S, 3S) -3-amino-2-hydroxy-4-phenylbutanoic acid; (2S,3S)-H-AHPBA), cyclic α-amino acids such as Thz ((R)-1,3-thiazolidine-4-carboxylic acid), Dmt ((R)-5,5-dimethyl-1,3-thiazolidine-4-carboxylic acid), Mox ((4S, 5R)-5-methyl-1,3-oxazolidine-4-carboxylic acid), Pip ((R)-pipecolic acid; (R)-2-piperidine carboxylic acid), and the like, as well as other α-amino acids, used as raw materials in the examples were previously prepared as amino acid N-protected derivatives of these compounds according to the method known in the art by publication, followed by release of the amino group. As other raw materials, acyl chlorides were used for Z group (benzyloxycarbonyl group), methoxycarbonyl group, and ethoxycarbonyl group; acid anhydrides were used for acetyl group; corresponding carboxylic acids or derivative thereof were used for acyl group such as methoxyacetyl group, ethoxyacetyl group, iQoa group (5-isoquinolyloxyacetyl group; 5-isoquinolyloxyethanoyl group), 2-chromonecarbonyl group (benzo-4-pyron-2-ylcarbonyl group; Chc), benzofuran-2-ylcarbonyl group (Bfc) and the like. In addition, some commercially available intermediate raw material compounds, such as amino acid derivatives of which the nitrogen was protected and modified by a Z group, were used.

EXAMPLES

Example 1

(R)-N-benzyl-3-{(2S,3S)-3-[N-(benzyloxycarbonyl)-L-asparaginyl]amino-2-hydroxy-4-phenylbutanoyl}-5,5-dimethyl-1,3-thiazolidine-4-carboxamide (Z-Asn-Apns-Dmt-NHBzl)

<Step 1>

(R)-3-tert-butoxycarbonyl-4N benzylcarbamoyl-5,5-dimethyl-1,3-thiazolidine (Boc-Dmt-NHBzl)

DPP-Cl (1.14 ml, 5.5 mmol) was added to a solution of Boc-Dmt-OH (1.31 g, 5.0 mmol) and Et₃N (0.76 ml, 5.5 mmol) in ethyl acetate (20 ml) while cooling with ice, and the mixture was stirred for one hour. After the addition of benzylamine (0.60 ml, 5.5 mmol) and Et₃N (0.76 ml, 5.5 mmol), the mixture was further stirred overnight. AcOEt was added to the reaction mixture, and the resulting mixture was washed with 3% Na₂CO₃ (twice), 1N HCl (twice), and 5% NaCl (once) and dried over MgSO₄. After filtration and concentration, the residue was recrystallized from AcOEt-n-hexane to obtain the title compound (1.46 g, 65%).

<Step 2>

(R)-N-benzyl-3-{(2S,3S)-3-[N-(benzyloxycarbonyl)-L-asparaginyl]amino-2-hydroxy-4-phenylbutanoyl}-5,5-dimethyl-1,3-thiazolidine-4-carboxamide (Z-Asn-Apns-Dmt-NHBzl)

4N HCl/dioxane (3 ml) was added to the compound Boc-Dmt-NHBzl (0.23 g, 0.65 mmol) obtained in the step 1 and the mixture was stirred for two hours. After concentration, the reaction mixture was dissolved in DMF (5 ml) and neutralized with Et₃N (0.11 ml). Z-Asn-Apns-OH (0.22 g), HOBt (68 mg), and EDC.HCl (105 mg) were added to this solution and the mixture was stirred overnight. H₂O (20 ml) was added to the reaction mixture. The precipitate was washed with 5% NaHCO₃ and H₂O and recrystallized from ethyl acetate to obtain the title compound (120 mg, 36%).

HPLC: 16.69 min

TOF-mass: 676 (M+1)

Example 2

(R)-N-(2-methylbenzyl)-3-{(2S,3S)-3-[N-(benzyloxycarbonyl)-L-asparaginyl]amino-2-hydroxy-4-phenylbutanoyl}-1,3-thiazolidine-4-carboxamide (Z-Asn-Apns-Thz-NHBzl(2-Me))

<Step 1>

(R)-N-(2-methylbenzyl)-1,3-thiazolidine-4-carboxamide (H-Thz-NHBzl(2-Me))

EDC.HCl (6.30 g, 33.0 mmol) was added to a solution of Boc-Thz-OH (6.99 g, 30 mmol), 2-methylbenzylamine (4.46 ml, 36.0 mmol), and HOBt (4.05 g, 30 mmol) in CH₂Cl₂ (100 ml) while cooling with ice, and the mixture was stirred overnight. The reaction mixture was washed with 3% Na₂CO₃ (twice), 1NHCl (once), and 5% NaCl (once) and dried over MgSO₄. After filtration and concentration, the residue was dissolved in CH₂Cl₂ (100 ml). After the addition of methanesulfonic acid MSA (5.86ml, 90mmol), the mixture was stirred for two hours. H₂O (150 ml) was added to the reaction mixture and the aqueous layer adjusted to pH 8 with Na₂CO₃ was extracted with CH₂Cl₂ (100 ml). The extract was washed with 5% NaCl and dried over MgSO₄. After filtration and concentration, the residue was recrystallized from AcOEt/n-hexane to obtain the title compound (6.04 g, 85%).

¹H-NMR (DMSO-d₆)

δ (ppm); 2.56(s, 3H), 2.85–3.05(m, 3H), 3.2–3.4(m, 1H), 3.86(m, 1H),4.0–4.2(m, 2H), 4.2–4.3(br, 2H), 7.0–7.2(br, 4H), 8.34(br, H)

TOF-Mass; 237 (M+1)

<Step 2>

(R)-N-(2-methylbenzyl)-3-{(2S,3S)-3-[N-(benzyloxycarbonyl)-L-asparaginyl]amino-2-hydroxy-4-phenylbutanoyl}-1,3-thiazolidine-4-carboxamide (Z-Asn-Apns-Thz-NHBzl(2-Me))

EDC.HCl (0.105 g) was added to a solution of H-Thz-NHBzl(2-Me) (0.12 g) obtained in the step 1, Z-Asn-Apns-OH (0.22 g), and HOBt (0.068 g) in DMF (5 ml) and the mixture was stirred overnight. After adding ethyl acetate, the reaction mixture was washed with 5% NaHCO₃, 1N HCl, and 5% NaCl and dried over MgSO₄. After filtration and concentration, the residue was recrystallized from n-hexane/ethyl acetate to obtain the title compound (183 mg).

TOF-Mass; 662 (M+1)

HPLC: 19.72 min

Example 3

(R)-N-(2-methylbenzyl)-3-{(2S,3S)-3-[N-(benzyloxycarbonyl)-L-asparaginyl]amino-2-hydroxy-4-phenylbutanoyl}-5,5-dimethyl-1,3-thiazolidine-4-carboxamide (Z-Asn-Apns-Dmt-NHBzl(2-Me))

<Step 1>

(R) -N- (2-methylbenzyl) -5, 5-dimethyl-1, 3-thiazolidine-4-carboxamide (H-Dmt-NHBzl(2-Me))

Under cooling with ice, DPP-Cl (2.28 ml, 11 mmol) was added to a solution of Boc-Dmt-OH (2.61 g, 10 mmol) and Et$_3$N (1.39 ml, 10 mmol) in DMF (10 ml), and the mixture was stirred for one hour. After the addition of 2-methylbenzylamine (1.36 ml, 11 mmol) and Et$_3$N (1.53 ml, 11 mmol), the mixture was stirred overnight. AcOEt was added to the reaction mixture and the mixture was washed with 3% Na$_2$CO$_3$ (twice), 1N HCl (twice), and 5% NaCl (once) and dried over MgSO$_4$. After filtration and concentration, the residue was dissolved in CH$_2$Cl$_2$ (25 ml) and 4N HCl/dioxane (25 ml, 100 mmol) was added to the mixture. The mixture was then stirred for three hours. After concentration, the residue was dissolved in H$_2$O and washed with toluene. The aqueous layer adjusted to pH 8 with 2N NaOH was extracted with CH$_2$Cl$_2$. The extract was washed with 5% NaCl and dried over MgSO$_4$. After filtration and concentration, the residue was recrystallized from AcOEt/n-hexane to obtain the title compound (1.90 g, 72%).

$^1$H-NMR (DMSO-d6) δ (ppm); 1.15(s, 3H), 1.52(s, 3H), 2.28(s, 3H), 3.27(s, 1H), 3.66(s, 1H), 4.03(d, 1H, J=9.6 Hz), 4.22–4.33(m, 3H), 7.12–7.22(m, 4H), 8.32–8.33(br, 1H)

TOF-Mass; 265 (M+1)

<Step 2<

(R)-N-(2-methylbenzyl)-3-{(2S,3S)-3-amino-2-hydroxy-4-phenylbutanoyl}-5,5-dimethyl-1,3-thiazolidine-4-carboxamide (H-Apns-Dmt-NHBzl(2-Me))

EDC.HCl (1.05 g, 5.5 mmol) was added to a solution of Boc-Apns-OH (1.48 g, 5.0 mmol), H-Dmt-NHBzl (2-Me) (1.45g, 5.5 mmol) obtained in the step 1, and HOBt (0.68 g, 5.0 mmol) in DMF (30 ml) and the mixture was stirred overnight. After the addition of AcOEt, the reaction mixture was washed with 3% Na$_2$CO$_3$, 1N HCl, and 5% NaCl and dried over MgSO$_4$. After filtration and concentration, 4N HCl/dioxane (25 ml, 100 mmol) was added to the residue, and the mixture was stirred for one hour. After concentration, the residue was dissolved in H$_2$O and washed with toluene. The precipitate obtained by adjusting the aqueous layer to pH 8 with 2N NaOH were separated by filtration and washing with water. The crystals were suspended in MeOH (20 ml), the suspension was heated and allowed to cool to produce a precipitate. The precipitate was collected by filtration and dried to obtain the title compound (1.60 g, 72%).

$^1$H-NMR (DMSO-d$_6$)

δ (ppm); 1.15–1.25(br, 2H), 1.34(s, 3H), 1.52(s, 3H), 2.16(s, 3H), 2.23–2.31(m, 1H), 2.70(t, 1H, J=10.0 Hz), 3.09(d, 1H, J=12.3 Hz), 4.04–4.08(br, 1H), 4.11(dd, 1H, J=5.0 Hz, 15.3 Hz), 4.22(dd, 1H, J=5.0 Hz, 15.0 Hz), 4.36(s, 1 H), 4.90(s, 2H), 5.31(d, 1H, J=6.6 Hz), 6.95(s, 3H), 7.12–7.31(m, 6H), 8.48(t, 1 H, J=4.8 Hz)

TOF-Mass; 442 (M+1)

<Step 3>

(R)-N-(2-methylbenzyl)-3-{(2S,3S)-3-[N-(benzyloxycarbonyl)-L-asparaginyl]amino-2-hydroxy-4-phenylbutanoyl}-5,5-dimethyl-1,3-thiazolidine-4-carboxamide (Z-Ans-Apns-Dmt-NHBzl(2-Me))

Elongation of the peptide chain was performed using H-Apns-Dmt-NHBzl(2-Me) (220 mg) obtained in the Step 2, Z-Asn-ONp (232 mg), HOBt (68 mg), and Et$_3$N (0.153 ml) to obtain the title compound (290 mg).

HPLC: 20.69 min

TOF-Mass; 690 (M+1)

Example 4

(R)-N-(2-methylbenzyl)-3-{(2S,3S)-3-[N-(benzyloxycarbonyl)-L-valyl]amino-2-hydroxy-4-phenylbutanoyl}-5,5-dimethyl-1,3-thiazolidine-4-carboxamide (Z-Val-Apns-Dmt-NHBzl(2-Me))

EDC.HCl (63 mg) was added to a solution of H-Apns-Dmt-NHBzl(2-Me) (132 mg) obtained in the Step 2 of Example 3, Z-Val-OH (75 mg), and HOBt (41 mg) in DMF (3 ml) and the mixture was stirred overnight. After the addition of ethyl acetate, the reaction mixture was washed with 5% Na$_2$CO$_3$, IN HCl, and 5% NaCl and dried over MgSO$_4$. After filtration and concentration, the residue was recrystallized from n-hexane/ethyl acetate to obtain the title compound (160 mg).

HPLC: 23.87 min

TOF-Mass; 675 (M+1)

Example 5

(R)-N-(2-chlorobenzyl)-3-{(2S,3S)-3-[N-(benzyloxycarbonyl)-L-asparaginyl]amino-2-hydroxy-4-phenylbutanoyl}-5,5-dimethyl-1,3-thiazolidine-4-carboxamide (Z-Asn-Apns-Dmt-NHBzl(2-Cl))

<Step 1>

(R)-N-(2-chlorobenzyl)-5,5-dimethyl-1,3-thiazolidine-4-carboxamide (H-Dmt-NHBzl(2-Cl))

DPP-Cl (2.28 ml, 11 mmol) was added to a solution of Boc-Dmt-OH (2.61 g, 10 mmol) and Et$_3$N (1.39 ml, 10 mmol) in DMF (10 ml) while cooling with ice and the mixture was stirred for one hour. After the addition of 2-chorobenzylamine (1.33 ml, 11 mmol) and Et$_3$N (1.53 ml, 11 mmol), the mixture was stirred overnight. AcOEt was added to the reaction mixture and the mixture was washed with 3% Na$_2$CO$_3$ (twice), 1N HCl (twice), and 5% NaCl (once) and dried over MgSO$_4$. After filtration and concentration, the residue was dissolved in CH$_2$Cl$_2$ (25 ml), and 4N HCl/dioxane (25 ml, 100 mmol) was added to the mixture followed by stirring for three hours. After concentration, H$_2$O was added to the residue. The resulting mixture was adjusted to pH 8 with 2N NaOH and extracted with CH$_2$Cl$_2$. The extract was washed with 5% NaCl and dried over MgSO$_4$. After filtration and concentration, the residue was recrystallized from AcOEt/n-hexane to obtain the title compound (1.51 g, 53%).

TOF-Mass; 285 (M+1)

<Step 2>

(R)-N-(2-chlorobenzyl)-3-{(2S,3S)-3-[N-(benzyloxycarbonyl)-L-asparaginyl]amino-2-hydroxy-4-phenylbutanoyl}-5,5-dimethyl-1,3-thiazolidine-4-carboxamide (Z-Asn-Apns-Dmt-NHBzl (2-Cl))

The title compound was synthesized from H-Dmt-NHBzl (2-Cl) (0.14 g) obtained in the step 1, Z-Asn-Apns-OH (0.22 g), HOBt (68 mg), and EDC.HCl (105 mg) according to the step 2 of Example 1 (287 mg).

HPLC: 20.89 min

TOF-Mass; 710 (M+1)

Example 6

(R)-N-(2-methylbenzyl)-3-{(2S,3S)-3-[N-(2-chromonecarbonyl)-L-asparaginyl]amino-2-hydroxy-4-phenylbutanoyl}-5,5-dimethyl-1,3-thiazolidine-4-carboxamide (Chc-Asn-Apns-Dmt-NHBzl(2-Me))

<Step 1>

(R)-N-(2-methylbenzyl)-3-{(2S,3S)-3-[N-(tert-butoxycarbonyl)-L-asparaginyl]amino-2-hydroxy-4-phenylbutanoyl}-5,5-dimethyl-1,3-thiazolidine-4-carboxamide (Boc-Asn-Apns-Dmt-NHBzl(2-Me))

HOBt (0.41 g), Boc-Asn-ONp (1.27 g), and $Et_3N$ (0.92 ml) were added to a solution of H-Apns-Dmt-NHBzl(2-Me) (1.32 g) obtained in the step 2 of Example 3 in DMF (20 ml) and the mixture was stirred overnight. After the addition of ethyl acetate, the reaction mixture was washed with 3% $NaHCO_3$, 1N HCl, and 5% NaCl and dried over $MgSO_4$. After filtration and concentration, the residue was recrystallized from AcOEt/n-hexane to obtain the title compound (1.79 g).

<Step 2>

(R)-N-(2-methylbenzyl)-3-{(2S,3S)-3-[N-(2-chromonecarbonyl)-L-asparaginyl]amino-2-hydroxy-4-phenylbutanoyl}-5,5-dimethyl-1,3-thiazolidine-4-carboxamide (Chc-Asn-Apns-Dmt-NHBzl(2-Me))

4N HCl/dioxane (2 ml) was added to Boc-Asn-Apns-Dmt-NHBzl(2-Me) (197 mg) obtained in the step 1 and the mixture was stirred for two hours. After concentration, the reaction mixture was dissolved in DMF (3 ml) and neutralized with $Et_3N$ (0.042 ml). After the addition of chromone-2-carboxylic acid (63 mg), HOBt (45 mg), and EDC.HCl (69 mg), the mixture was stirred overnight. Ethyl acetate was added to the reaction mixture and the mixture was washed with 3% $NaHCO_3$, 1N HCl, and 5%NaCl and dried over $MgSO_4$. After filtration and concentration, the residue was purified using silica gel column chromatography and reprecipitated from ethyl acetate/n-hexane to obtain the title compound (86 mg).

HPLC: 20.89 min

TOF-Mass; 728 (M+1)

Example 7

(R)-N-(2-methylbenzyl)-3-{(2S,3S)-3-[N-(2-benzofurancarbonyl)-L-asparaginyl]amino-2-hydroxy-4-phenylbutanoyl}-5,5-dimethyl-1,3-thiazolidine-4-carboxamide (Bfc-Asn-Apns-Dmt-NHBzl(2-Me))

4N HCl/dioxane (2 ml) was added to Boc-Asn-Apns-Dmt-NHBzl( 2-Me) (197 mg) obtained in the step 1 of Example 6 and the mixture was stirred for two hours. After concentration, the reaction mixture was dissolved in DMF (3 ml) and neutralized with $Et_3N$ (0.042 ml). 2-benzofurancarboxylic acid (54 mg), HOBt (45 mg), and EDC.HCl (69 mg) were added to this solution, and the mixture was stirred overnight. After the addition of ethyl acetate, the reaction mixture was washed with 3% $NaHCO_3$, 1N HCl, and 5% NaCl and dried over $MgSO_4$. After filtration and concentration, the residue was purified using silica gel column chromatography and reprecipitated from ethyl acetate/n-hexane to obtain the title compound (108 mg).

HPLC: 20.66 min

TOF-Mass; 700 (M+1)

Example 8

(R)-N-(2-methylbenzyl)-3-{(2S,3S)-3-[N-(5-isoquinolinyloxyacetyl)-L-valyl]amino-2-hydroxy-4-phenylbutanoyl}-5,5-dimethyl-1,3-thiazolidine-4-carboxamide (iQoa-Val-Apns-Dmt-NHBzl(2-Me))

<Step 1>

(R)-N-(2-methylbenzyl)-3-{(2S,3S)-3-[N-(tert-butoxycarbonyl)-L-valyl]amino-2-hydroxy-4-phenylbutanoyl}-5,5-dimethyl-1,3-thiazolidine-4-carboxamide (Boc-Val-Apns-Dmt-NHBzl(2-Me))

Boc-Val-OH (0.68 g), HOBt (0.43 g), and EDC.HCl (0.60 g) were added to a solution of H-Apns-Dmt-NHBzl (2-Me) (1.32 g) obtained in the step 2 of Example 3 in DMF (10 ml)and the mixture was stirred overnight. After the addition of ethyl acetate, the reaction mixture was washed with 3% $NaHCO_3$, 1N HCl, and 5% NaCl and dried over $MgSO_4$. After filtration and concentration, the residue was recrystallized from ethyl acetate/n-hexane to obtain the title compound (1.82 g).

HPLC: 23.54 min

<Step 2>

(R)-N-(2-methylbenzyl)-3-{(2S,3S)-3-(L-valyl)amino-2-hydroxy-4-phenylbutanoyl}-5,5-dimethyl-1,3-thiazolidine-4carboxamide (H-Val-Apns-Dmt-NHBzl(2-Me))

4N HCl/dioxane (14 ml) was added to Boc-Val-Apns-Dmt-NHBzl (2-Me) (1.79 g) obtained in the step 1 and the mixture was stirred for two hours. After concentration, the reaction mixture was dissolved in $CH_2Cl_2$ and washed with 3% $K_2CO_3$ and 5% NaCl and dried over $MgSO_4$. After filtration and concentration, the residue was recrystallized from ethyl acetate/n-hexane to obtain the title compound (1.35g).

HPLC: 16.26 min

<Step 3>

(R)-N-(2-methylbenzyl)-3-{(2S,3S)-3-[N-(5-isoquinolinyloxyacetyl)-L-valyl]amino-2-hydroxy-4-phenylbutanoyl}-5,5-dimethyl-1,3-thiazolidine-4-carboxamide (iQoa-Val-Apns-Dmt-NHBzl(2-Me))

5-isoquinolinyloxyacetic acid (64 mg), HOBt (43 mg), and EDC.HCl (60 mg) were added to H-Val-Apns-Dmt-NHBzl(2-Me) (162 mg) obtained in the step 2 and the mixture was stirred overnight. After the addition of ethyl acetate, the reaction mixture was washed with 3% $NaHCO_3$ and 5% NaCl and dried over $MgSO_4$. After filtration and concentration, the residue was reprecipitated from ethyl acetate/n-hexane to obtain the title compound (168 mg).

HPLC: 17.74 min

TOF-Mass; 726 (M+1)

Example 9

(4S,5R)-N-(2-methylbenzyl)-3-{(2S,3S)-3-[N-(benzyloxycarbonyl)-L-asparaginyl]amino-2-hydroxy-4-phenylbutanoyl}-5-methyl-1,3-oxazolidine-4-carboxamide (Z-Asn-Apns-Mox-NHBzl(2-Me))

<Step 1>

(4S,5R)-3-tert-butoxycarbonyl-5-methyl-1,3-oxazolidine-4-carboxylic acid(Boc-Mox-OH)

2N NaOH (10 ml) and HCHO (35%, 2.11 ml) were added to threonine H-Thr-OH (2.38 g, 20 mmol) and the mixture was stirred for two hours. After the addition of NH$_2$OH-HCl (0.14 g, 2 mmol), 2N NaOH (1 ml), Acetone (12 ml), and Boc$_2$O (4.82 g, 22 mmol), the mixture was stirred for six hours at room temperature. Next, H$_2$O (50 ml) and toluene (50 ml) were added and the organic layer was removed. After acetone was removed by distillation, the pH of the mixture was adjusted to 3 with 5% citric acid and the mixture was extracted with AcOEt (300 ml). The extract was washed with 5% NaCl (100 ml) and dried over MgSO$_4$. The dried material was subjected to concentration to obtain the title compound (4.15 g, 90%).

<Step 2>

(4S,5R)-3-tert-butoxycarbonyl-4-N-(2-methylbenzyl)carbamoyl-5-methyl-1,3-oxazolidine (Boc-Mox-NHBzl(2-Me))

HOSU (1.64 g, 14.3 mmol) and EDC·HCl (2.74 g, 14.3 mml) were added to a solution of Boc-Mox-OH (3.14 g, 13.6 mmol) obtained in the step 1 in dichloromethane (40 ml) while cooling with ice, and the mixture was stirred for two hours at room temperature. After 2-methylbenzylamine (3.37 ml, 27.2 mmol) was added while cooling with ice, the mixture was stirred for five hours at room temperature. The mixture was then washed with 1N HCl (50 ml) (twice), 5% NaHCO$_3$ (50 ml) (twice), and 5% NaCl (50 ml) (once) and dried over MgSO$_4$. After filtration and concentration, the title compound (3.60 g, 79%) was obtained.

<Step 3>

(4S,5R)-N-(2-methylbenzyl)-3-{(2S,3S)-3-[N-(benzyloxycarbonyl)-L-asparaginyl]amino-2-hydroxy-4-phenylbutanoyl}-5-methyl-1-oxazolidine-4-carboxamide (Z-Asn-Apns-Mox-NHBzl(2-Me))

4N HCl/dioxane (1.5 ml) was added to Boc-Mox-NHBzl (2-Me) (100 mg, 0.3 mmol) obtained in the step 2 while cooling with ice and the mixture was stirred for three hours at room temperature. After concentration, the residue was dissolved in DMF (1 ml) and neutralized with Et$_3$N (0.04 ml). Z-Asn-Apns-OH (140 mg, 0.32 mmol), HOBt (43 mg, 0.32 mmol), and EDC·HCl (60 mg, 0.32 mmol) were added to this solution while cooling with ice, and the mixture was stirred overnight at room temperature. After the addition of AcOEt (15 ml), the mixture was washed with 5% NaHCO$_3$ (10 ml, twice), 5% citric acid (10 ml, twice), and 5% NaCl (10 ml, once) and dried over MgSO$_4$. After filtration and concentration, the mixture was purified using silica column chromatography (eluent: dichloromethane-methanol) to obtain the title compound (70 mg, 35%).

HPLC: 19.30 min

TOF-Mass; 661 (M+1)

Example 10

(R)-N-(2-methylbenzyl)-3-{(2S,3S)-3-[N-(benzyloxycarbonyl)-L-asparaginyl]amino-2-hydroxy-4-phenylbutyl}-pyrrolidine-2-carboxamide (Z-Asn-AHPBA[CH$_2$N]-Pro-NHBzl(2-Me))

<Step 1>

(R)-N-(2-methylbenzyl)-3-{(2S,3S)-3-tert-butoxyformamide-2-hydroxy-4-phenylbutyl}-pyrrolidine-2-carboxamide (Boc-AHPBA[CH$_2$N]-Pro-NHBzl (2-Me))

A solution of (S)-N-(2-methylbenzyl)-pyrrolidine-2-carboxamide (0.64 g, 2.9 mmol) in isopropyl alcohol (3 ml) was added to a solution of 3(S)-(tert-butoxyformamide)-1,2(S)-epoxy-4-phenylbutane (0.26 g, 1 mmol) in iso-propyl alcohol (3 ml) while cooling with ice and the mixture was refluxed for four hours. After the addition of dichloromethane (20 ml), the mixture was washed with 5% NaHCO$_3$ (20 ml), 5% citric acid (20 ml), and 5% NaCl (20ml) and dried over MgSO$_4$. After filtration and concentration, the mixture was recrystallized from AcOEt/hexane to obtain the title compound (237 mg, 49%).

<Process 2>

(R)-N-(2-methylbenzyl)-3-{(2S,3S)-3-[N-(benzyloxycarbonyl)-L-asparaginyl]amino-2-hydroxy-4-phenylbutyl}-pyrrolidine-2-carboxamide (Z-Asn-AHPBA[CH$_2$N]Pro-NHBzl (2-Me))

4N HCl/dioxane (1.5 ml, 6 mmol) was added to Boc-AHPBA[CH$_2$N]Pro-NHBzl(2-Me) (144 mg, 0.3 mmol) obtained in the step 1 and the mixture was stirred for one hour at room temperature. After concentration, the mixture was dissolved in DMF (2 ml) and neutralized with Et$_3$N (0.04 ml) while cooling with ice. Z-Asn-ON p (174 mg, 0.45 mmol) and Et$_3$N (0.1 ml) were added while cooling with ice and the mixture was stirred overnight at room temperature. After the addition of ethyl acetate (20 ml), the mixture was washed with 5% NaHCO$_3$ (20 ml, five times) and 1N HCl (20 ml). A white-colored precipitate separated by filtration was dried to obtain the title compound (172 mg, 91%).

HPLC: 17.78 min

TOF-Mass; 631 (M+1)

Example 11

(R)-N-(2-methylbenzyl)-3-{(2S,3S)-3-[N-(2-benzofurancarbonyl)-L-valyl]amino-2-hydroxy-4-phenylbutanoyl}-5,5-dimethyl-1,3-thiazolidine-4-carboxamide (Bfc-Val-Apns-Dmt-NHBzl(2-Me))

EDC·HCl (60 mg) was added to a solution of H-Val-Apns-Dmt-NHBzl(2-Me) (162 mg) obtained in the step 2 of Example 8, 2-benzofurancarboxylic acid (51 mg), and HOBt (43 mg) in DMF (5 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was purified using silica gel column chromatography and reprecipitated from ethyl acetate/n-hexane to obtain the title compound (88 mg).

HPLC: 23.44 min

TOF-Mass; 685 (M+1)

Example 12

(R)-N-(2-methylbenzyl)-3-{(2S,3S)-3-[N-(2-chromonecarbonyl)-L-valyl]amino-2-hydroxy-4-phenylbutanoyl}-5,5-dimethyl-1,3-thiazolidine-4-carboxamide (Chc-Val-Apns-Dmt-NHBzl(2-Me))

EDC.HCl (63 mg) was added to a solution of H-Val-Apns-Dmt-NHBzl (2-Me) (162 mg) obtained in the step 2 of Example 8, 2-chromonecarboxylic acid (57 mg), and HOBt (41 mg) in DMF (5 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was purified using a silica gel column chromatography and reprecipitated from ethyl acetate/n-hexane to obtain the title compound (165 mg).

HPLC: 21.69 min
TOF-Mass; 713 (M+1)

Example 13

(R)-N-(2-methylbenzyl)-3-{(2S,3S)-3-[N-(2-quinolinecarbonyl)-L-valyl]amino-2-hydroxy-4-phenylbutanoyl}-5,5-dimethyl-1,3-thiazolidine-4-carboxamide (2-Quic-Val-Apns-Dmt-NHBzl(2-Me))

EDC.HCl (42 mg) was added to a solution of H-Val-Apns-Dmt-NHBzl(2-Me) (108 mg) obtained in the step 2 of Example 8, 2-quinolinecarboxylic acid (38 mg), and HOBt (27 mg) in DMF (5 ml) and the mixture was stirred overnight. After the addition of ethyl acetate, the reaction mixture was washed with 3% $Na_2CO_3$ and 5% NaCl and dried over $MgSO_4$. After filtration and concentration, the residue was purified using silica gel column chromatography and recrystallized from dichloromethane/n-hexane to obtain the title compound (53 mg).
HPLC: 24.52 min
TOF-Mass; 696 (M+1)

Example 14

(R)-N-(2-methylbenzyl)-3-{(2S,3S)-3-[N-(2-benzothiazolecarbonyl)-L-valyl]amino-2-hydroxy-4-phenylbutanoyl}-5,5-dimethyl-1,3-thiazolidine-4-carboxamide (Btc-Val-Apns-Dmt-NHBzl(2-Me))

EDC.HCl (46 mg) was added to a solution of H-Val-Apns-Dmt-NHBzl (2-Me) (108 mg) obtained in the step 2 of Example 8, 2-benzothiazolecarboxylic acid (36 mg), and HOBt (27 mg) in DMF (5 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography and reprecipitated with ethyl acetate/n-hexane to obtain the title compound (91 mg).
HPLC: 25.89 min
TOF-Mass; 702 (M+1)

Example 15

(R)-N-(2-methylbenzyl)-3-{(2S,3S)-3-[N-(2-benzimidazolecarbonyl)-L-valyl]amino-2-hydroxy-4-phenylbutanoyl}-5,5-dimethyl-1,3-thiazolidine-4-carboxamide (Bic-Val-Apns-Dmt-NHBzl(2-Me))

EDC.HCl (42 mg) was added to a solution of H-Val-Apns-Dmt-NHBzl(2-Me) (108 mg) obtained in the step 2 of Example 8, 2-benzimidazolecarboxylic acid (32 mg), and HOBt (27 mg) in DMF (5 ml) and the mixture was stirred overnight. After the addition of ethyl acetate, the reaction mixture was washed with 3% $Na_2CO_3$ and 5% NaCl and dried over $MgSO_4$. After filtration and concentration, the residue was purified using silica gel column chromatography to obtain the title compound (73 mg).
HPLC: 27.48 min
TOF-Mass; 685 (M+1)

Example 16

(R)-N-(2-methylbenzyl)-3-{(2S,3S)-3-[N-(7-methoxybenzofuran-2-carbonyl)-L-valyl]amino-2-hydroxy-4-phenylbutanoyl}-5,5-dimethyl-1,3-thiazolidine-4-carboxamide ((7-MeO)Bfc-Val-Apns-Dmt-NHBzl(2-Me))

EDC.HCl (60 mg) was added to a solution of H-Val-Apns-Dmt-NHBzl (2-Me) (162 mg) obtained in the step 2 of Example 8, 7-methoxybenzofuran-2-carboxylic acid (60 mg), and HOBt (43 mg) in DMF (5 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography to obtain the title compound (198 mg).
HPLC: 23.49 min
TOF-Mass; 715 (M+1)

Example 17

(R)-N-(2-methylbenzyl)-3-{(2S,3S)-3-[N-(3-benzylphenoxyacetyl)-L-valyl]amino-2-hydroxy-4-phenylbutanoyl}-5,5-dimethyl-1,3-thiazolidine-4-carboxamide ((3-Bzl)Phoa4-Val-Apns-Dmt-NHBzl(2-Me))

4N HCl/dioxane (2 ml) was added to Boc-Val-Apns-Dmt-NHBzl(2-Me) (197 mg) obtained in the step 1 of Example 8 and the mixture was stirred for two hours. After concentration, the reaction mixture was dissolved in DMF (3 ml) and neutralized with $Et_3N$ (0.047 ml). 3-benzylphenoxyacetic acid (80 mg), HOBt (45 mg), and EDC.HCl (69 mg) were added to this solution and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography and reprecipitated from ethyl acetate/n-hexane to obtain the title compound (155 mg).
HPLC: 23.94 min
TOF-Mass; 780 (M+1)

Example 18

(R)-N-(2-methylbenzyl)-3-{(2S,3S)-3-[N-(2-quinoxalinecarbonyl)-L-asparaginyl]amino-2-hydroxy-4-phenylbutanoyl}-5,5-dimethyl-1,3-thiazolidine-4-carboxamide (2-Qxc-Asn-Apns-Dmt-NHBzl(2-Me))

4N HCl/dioxane (2 ml) was added to Boc-Asn-Apns-Dmt-NHBzl( 2-Me) (131 mg) obtained in the step 1 of Example 6 and the mixture was stirred for two hours. After concentration, the reaction mixture was dissolved in DMF (3 ml) and neutralized with $Et_3N$ (0.031 ml). 2-quinoxalinecarboxylic acid (38 mg), HOBt (30 mg), and EDC.HCl (46 mg) were added to this solution and the mixture was stirred overnight. After the addition of ethyl acetate, the reaction mixture was washed with 3% $Na_2CO_3$ and 5% NaCl and dried over $MgSO_4$. After filtration and concentration, the residue was purified using silica gel column chromatography and reprecipitated from ethyl acetate/n-hexane to obtain the title compound (105 mg).
HPLC: 20.01 min
TOF-Mass; 713 (M+1)

Example 19

(R)-N-(2-methylbenzyl)-3-{(2S,3S)-3-[N-(2-quinoxalinecarbonyl)-L-valyl]amino-2-hydroxy-4-phenylbutanoyl}-5,5-dimethyl-1,3-thiazolidine-4-carboxamide (2-Qxc-Val-Apns-Dmt-NHBzl(2-Me))

EDC.HCl (69 mg) was added to a solution of H-Val-Apns-Dmt-NHBzl (2-Me) (162 mg) obtained in the step 2 of Example 8, 2-quinoxalinecarboxylic acid (57 mg), and HOBt (45 mg) in DMF (5 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography and reprecipitated from ethyl acetate/n-hexane to obtain the title compound (109 mg).

HPLC: 24.41 min

TOF-Mass; 698 (M+1)

Example 20

(R)-N-(2-methylbenzyl)-3-{(2S,3S)-2-hydroxy-3-[(S)-2-(7-methoxy-2-benzofurancarbonyl)aminopropanoyl]amino-4-phenylbutanoyl}-5,5-dimethyl-1,3-thiazolidine-4-carboxamide ((7-MeO)Bfc-Ala-Apns-Dmt-NHBzl(2-Me))

EDC.HCl (58 mg) was added to a solution of H-Ala-Apns-Dmt-NHBzl(2-Me).HCl (150 mg), triethylamine (38 μl), 7-methoxy-2-benzofurancarboxylic acid (51 mg), and HOBt (37 mg) in DMF (5 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography and reprecipitated with ethyl acetate/n-hexane to obtain the title compound (98 mg).

HPLC: 22.02 min

TOF-Mass; 687 (M+1)

Example 21

(R)-N-(2-methylbenzyl)-3-{(2S,3S)-2-hydroxy-3-[(S)-2-(3-quinolinecarbonyl)amino-3-methylbutanoyl]amino-4-phenylbutanoyl}-5,5-dimethyl-1,3-thiazolidine-4-carboxamide (3-Quic-Val-Apns-Dmt-NHBzl(2-Me))

EDC.HCl (69 mg) was added to a solution of H-Val-Apns-Dmt-NHBzl (2-Me) (162 mg) obtained in the step 2 of Example 8, 3-quinolinecarboxylic acid (57 mg), and HOBt (45 mg) in DMF (5 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography and reprecipitated from ethyl acetate/n-hexane to obtain the title compound (155 mg).

HPLC: 19.66 min

TOF-Mass; 696 (M+1)

Example 22

(R)-N-(2-methylbenzyl)-3-{(2S,3S)-2-hydroxy-3-[(S)-2-(3-dimethylaminophenoxyacetyl)amino-3-methylbutanoyl]amino-4-phenylbutanoyl}-5,5-dimethyl-1,3-thiazolidine-4-carboxamide ((3-Me$_2$N)Phoa-Val-Apns-Dmt-NHBzl (2-Me))

EDC.HCl (69 mg) was added to a solution of H-Val-Apns-Dmt-NHBzl (2-Me) (162 mg) obtained in the step 2 of Example 8, 3-dimethylaminophenoxyacetic acid (64 mg), and HOBt (45 mg) in DMF (5 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography and reprecipitated from ethyl acetate/n-hexane to obtain the title compound (106 mg).

HPLC: 18.77 min

TOF-Mass; 718 (M+1)

$^1$H-NMR (DMSO-d$_6$):

δ (ppm); 0.70(d, 6H, J=6.5 Hz), 1.36(s, 3H), 1.50(s, 3 H), 1.90(m, 1H), 2.23(s, 3H), 2.6–2.8(m, 2H), 2.85(s, 6H), 4.13–4.20(m, 3H), 4.38–4.50(m, 5 H), 4.94(d, 1H, J=9.2 Hz), 5.06(d, 1H, J=8.6 Hz), 5.28(d, 1H, J=7.3 Hz), 6.20–6.24(m, 2 H), 6.33(d, 1H, J=8.1 Hz), 7.0–7.4(m, 10H), 7.61(d, 1H, J=9.2 Hz), 8.14(d, 1 H, J=7.8 Hz), 8.37(t, 1H)

Example 23

(R)-N-(2-methylbenzyl)-3-{(2S,3S)-2-hydroxy-3-[(S)-2-(5-quinolinyloxyacetyl)amino-3-methylbutanoyl]amino-4-phenylbutanoyl}-5,5-dimethyl-1,3-thiazolidine-4-carboxamide (5-Qoa-Val-Apns-Dmt-NHBzl(2-Me))

EDC.HCl (63 mg) was added to a solution of H-Val-Apns-Dmt-NHBzl(2-Me) (162 mg) obtained in the step 2 of Example 8, 5-quinolinyloxyacetic acid (64 mg), and HOBt (43 mg) in DMF (5 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography to obtain the title compound (140 mg).

HPLC: 17.81 min

TOF-Mass; 726 (M+1)

Example 24

(R)-N-(2-methylbenzyl)-3-{(2S,3S)-2-hydroxy-3-[(S)-2-(6-quinolinyloxyacetyl)aminobutanoyl]amino-4-phenylbutanoyl}-5,5-dimethyl-1-thiazolidine-4-carboxamide (6-Qoa-Abu-Apns-Dmt-NHBzl(2-Me))

EDC.HCl (63 mg) was added to a solution of H-Abu-Apns-Dmt-NHBzl(2-Me) (158 mg), 6-quinolinyloxyacetic acid (64 mg), and HOBt (43 mg) in DMF (5 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography to obtain the title compound (170 mg).

HPLC: 17.30 ml

TOF-Mass; 712 (M+1)

Example 25

(R)-N-(2-methylbenzyl)-3-{(2S,3S)-2-hydroxy-3-[(S)-2-(3-dimethylaminophenoxyacetyl)aminobutanoyl]amino-4-phenylbutanoyl}-5,5-dimethyl-1-thiazolidine-4-carboxamide ((3-Me$_2$N)Phoa-Abu-Apns-Dmt-NHBzl (2-Me))

EDC.HCl (81 mg) was added to a solution of H-Abu-Apns-Dmt-NHBzl(2-Me) (210 mg), 3-dimethylaminophenoxyacetic acid (78 mg), and HOBt (57 mg) in DMF (5 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography to obtain the title compound (130 mg).

HPLC: 17.92 min
TOF-Mass; 704 (M+1)

Example 26

(R)-N-(2-methylbenzyl)-3-{(2S,3S)-2-hydroxy-3-[(S)-2-(3-dimethylaminophenoxyacetyl)aminopropanoyl]amino-4-phenylbutanoyl}-5,5-dimethyl-1,3-thiazolidine-4-carboxamide ((3-Me$_2$N)Phoa-Ala-Apns-Dmt-NHBzl(2-Me))

EDC.HCL (63 mg) was added to a solution of H-Ala-Apns-Dmt-NHBzl(2-Me).HCl (153 mg), triethylamine (42 µl), 3-dimethylaminophenoxyacetic acid (59 mg), and HOBt (41 mg) in DMF (5 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was purified using silica gel column chromatography and reprecipitated from ethyl acetate/n-hexane to obtain the title compound (130 mg).

HPLC: 17.51 min
TOF-Mass; 690 (M+1)

Example 27

(R)-N-(2-methylbenzyl)-3-{(2S,3S)-2-hydroxy-3-[(S)-2-(methoxycarbonyl)amino-3-methylbutanoyl]amino-4-phenylbutanoyl}-5,5-dimethyl-1,3-thiazolidine-4-carboxamide (MeO-CO-Val-Apns-Dmt-NHBzl(2-Me))

Methyl chloroformate (85 µl) and triethylamine (139 µl) were added to a solution of H-Val-Apns-Dmt-NHBzl (2-Me) (540 mg) obtained in the step 2 of Example 8 in ethyl acetate (4 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was reprecipitated from ethyl acetate/n-hexane to obtain the title compound (448 mg).

HPLC: 20.38 min
TOF-Mass; 599 (M+1)
$^1$H-NMR (DMSO-d$_6$):

δ (PPm); 0.65(d, 3H, J=6.8 Hz), 0.70(d, 3H, J=6.8 Hz), 1.36(s, 3 H), 1.50(s, 3 H), 1.80(m, 1H), 2.27(s, 3H), 2.67(m, 2H), 3.52(s, 3H), 3.74(t, 1H), 4.16(dd, 2H, J=4.3 Hz, 15 Hz), 4.40(d, 2H, J=6.8 Hz), 4.50(s, 1H), 4.93(d, 1H, J=9.5 Hz), 5.05(d, 1H, J=9.5 Hz), 5.25(d, 1H, J=6.8 Hz), 7.09–7.32(m, 10H), 7.88(d, 1H, J=8.4 Hz), 8.36(t, 1 H)

Example 28

(R)-N-(2-methylbenzyl)-3-{(2S,3S)-2-hydroxy-3-[(S)-2-(methoxycarbonyl)aminobutanoyl]amino-4-phenylbutanoyl}-5,5-dimethyl-1,3-thiazolidine-4-carboxamide (MeO-CO-Abu-Apns-Dmt-NHBzl(2-Me))

Methyl chloroformate (26 µl) and triethylamine (46 µl) were added to a solution of H-Abu-Apns-Dmt-NHBzl (2-Me) (158 mg) in ethyl acetate (3 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was purified using silica gel column chromatography and reprecipitated from ethyl acetate/n-hexane to obtain the title compound (144 mg)

HPLC: 19.68 min
TOF-Mass; 585 (M+1)

Example 29

(R)-N-(2-methylbenzyl)-3-{(2S,3S)-2-hydroxy-3-[(S)-2-(ethoxycarbonyl)amino-3-methylbutanoyl]amino-4-phenylbutanoyl}-5,5-dimethyl-1,3-thiazolidine-4-carboxamide (EtO-CO-Val-Apns-Dmt-NHBzl(2-Me))

Ethyl chloroformate (32 µel), triethylamine (46 µl) were added to a solution of H-Val-Apns-Dmt-NHBzl(2-Me) (162 mg) obtained in the step 2 of Example 8 in ethyl acetate (3 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was purified using silica gel column chromatography and reprecipitated from ethyl acetate/n-hexane to obtain the title compound (149 mg).

HPLC: 21.17 min
TOF-Mass; 613 (M+1)

Example 30

(R)-N-(2-methylbenzyl)-3-{(2S,3S)-2-hydroxy-3-[(S)-2-(methoxyethoxycarbonyl)amino-3-methylbutanoyl]amino-4-phenylbutanoyl}-5,5-dimethyl-1,3-thiazolidine-4-carboxamide (MeO-(CH$_2$)$_2$-O-CO-Val-Apns-Dmt-NHBzl (2-Me))

<Step 1>

Methoxyethyl p-nitrophenyl carbonate

P-nitrophenyl chloroformate (2.01 g) was added to a solution of methoxyethanol (790 µl) in pyridine (10 ml) and the mixture was stirred overnight. After concentration, the reaction mixture was dissolved in methylene chloride and was washed with 1N HCl and 5% NaCl and dried over MgSO$_4$. After filtration and concentration, the title compound (2.48 g) was obtained.

<Step 2>

(R)-N-(2-methylbenzyl)-3-{(2S,3S)-2-hydroxy-3-[(S)-2 -(methoxyethoxycarbonyl)amino-3-methylbutanoyl]amino-4-phenylbutanoyl}-5,5-dimethyl-1,3-thiazolidine-4-carboxamide Methoxyethyl p-nitrophenyl carbonate (112 mg), HOBt (41 mg), triethylamine (104 µl) were added to a solution of H-Val-Apns-Dmt-NHBzl(2-Me) obtained in the step 2 of Example 8 in DMF (5 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was purified using silica gel column chromatography and reprecipitated from ethyl acetate/n-hexane to obtain the title compound (130 mg).

HPLC: 20.36 min
TOF-Mass; 643 (M+1)

Example 31

(R)-N-(2-methylbenzyl)-3-{(2S,3S)-2-hydroxy-3-[(S)-2-(methoxyacetyl)amino-3-methylbutanoyl]amino-4-phenylbutanoyl}-5,5-dimethyl-1,3-thiazolidine-4-carboxamide (MeO-CH$_2$-CO-Val-Apns-Dmt-NHBzl(2-Me))

Methoxyacetic acid (23 µl), HOBt (48 mg), and EDC.HCl (63 mg) were added to a solution of H-Val-Apns-Dmt- NHBzl(2-Me) (162 mg) obtained in the step 2 of Example 8 in DMF (5 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was recrystallized from ethyl acetate/n-hexane to obtain the title compound (149 mg).

HPLC: 20.01 min

TOF-Mass; 613 (M+1)

$^1$H-NMK (DMSO-d$_6$):

δ (ppm); 0.67(d, 3H, J=6.5 Hz), 0.74(d, 3H, J=6.2 Hz), 1.36(s, 3 H), 1.50(s, 3H), 1.89(m, 1H), 2.27(s, 3H), 2.68(m, 2H), 3.29(s, 3H), 3.81(s, 2H), 4.13–4.20(m, 3H), 4.38–4.41 (m, 2H), 4.51(s, 1H), 4.94(d, 1H, J=8.6 Hz), 5.05(d, 1H, J=8.9 Hz), 5.25(d, 1H, J=7.0 Hz), 7.09–7.41(m, 10 H), 8.17(d, 1H, J=8.41 Hz), 8.39(t, 1H)

Example 32

(R)-N-(2-methylbenzyl)-3-{(2S,3S)-2-hydroxy-3-[(S)-2-(ethoxyacetyl)amino-3-methylbutanoyl]amino-4-phenylbutanoyl}-5,5-dimethyl-1,3-thiazolidine-4-carboxamide (EtO-CH$_2$-CO-Val-Apns-Dmt-NHBzl(2-Me))

Ethoxyacetic acid (28 μl), HOBt (41 mg), and HDC.HCl (63 mg) were added to a solution of H-Val-Apns-Dmt-NHBzl(2-Me) (162 mg) obtained in the step 2 of Example 8 in DMF (5 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was recrystallized from ethyl acetate/n-hexane to obtain the title compound (153 mg).

HPLC: 20.88 min

TOF-Mass; 627 (M+1)

Example 33

(R)-N-(2-methylbenzyl)-3-{(2S,3S)-2-hydroxy-3-[(S)-2-acetylamino-3-methylbutanoyl]amino-4-phenylbutanoyl}-5,5-dimethyl-1,3-thiazolidine-4-carboxamide (Ac-Val-Apns-Dmt-NHBzl(2-Me))

Acetic anhydride (31 μl) and triethylamine (46 μl) were added to a solution of H-Val-Apns-Dmt-NHBzl(2-Me) (162 mg) obtained in the step 2 of Example 8 in ethyl acetate (5 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was reprecipitated from ethyl acetate/n-hexane to obtain the title compound (143 mg).

HPLC: 19.32 min

TOF-Mass; 583 (M+1)

Example 34

(R)-N-(2-methylbenzyl)-3-{(2S,3S)-2-hydroxy-3-[(S)-2-acetylaminobutanoyl]amino-4-phenylbutanoyl}-5,5-dimethyl-1,3-thiazolidine-4-carboxamide (Ac-Abu-Apns-Dmt-NHBzl(2-Me))

Acetic anhydride (31 μl) and triethylamine (46 μl) were added to a solution of H-Abu-Apns-Dmt-NHBzl(2-Me) (158 mg) in ethyl acetate (5 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was reprecipitated from ethyl acetate/n-hexane to obtain the title compound (136 mg).

HPLC: 18.68 min

TOF-Mass; 569 (M+1)

Example 35

(R)-N-tert-butyl-3-{(2S,3S)-2-hydroxy-3-[(S)-2-(3-dimethylaminophenoxyacetyl)amino-3-methylbutanoyl]amino-4-phenylbutanoyl}-5,5-dimethyl-1,3-thiazolidine-4-carboxamide ((3-Me$_2$N) Phoa-Val-Apns-Dmt-NHtBu)

<Step 1>

(R)-N-tert-butyl-3-{(2S,3S)-2-hydroxy-3-[(S)-2-(tert-butoxycarbonyl)amino-3-methylbutanoyl]amino-4-phenylbutanoyl}-5,5-dimethyl-1,3-thiazolidine-4-carboxamide (Boc-Val-Apns-Dmt-NHtBu)

EDC.HCl (211 mg) was added to a solution of H-Apns-Dmt-NHtBu (393 mg), Boc-Val-OH (203 mg), and HOBt (135 mg) in DMF (3 ml) and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was reprecipitated from ethyl acetate/n-hexane to obtain the title compound (556 mg).

<Step 2>

(R)-N-tert-butyl-3-{(2S,3S)-2-hydroxy-3-[(S)-2-(3-dimethylaminophenoxyacetyl)amino-3-methylbutanoyl]amino-4-phenylbutanoyl}-5,5-dimethyl-1,3-thiazolidine-4-carboxamide ((3-Me$_2$N) Pboa-Val-Apns-Dmt-NHtBu)

The compound Boc-Val-Apns-Dmt-NHtBu (148 mg) obtained in the step 1 was treated with 4N HCl/dioxane for two hours at room temperature. After concentration, the mixture was dissolved in DMF and neutralized with Et$_3$N (37 ml). 3-dimethylaminophenoxyacetic acid (51 mg), HOBt (35 mg), and EDC.HCl (53 mg) were added to a solution of the resulting H-Val-Apns-Dmt-NHtBu in DMF and the mixture was stirred overnight. After the addition of ethyl acetate, the reaction mixture was washed with 3% Na$_2$CO$_3$, 1N HCl, and 5% NaCl and dried over MgSO$_4$. After filtration and concentration, the residue was purified using silica gel column chromatography to obtain the title compound (130 mg).

HPLC: 17.65 min

TOF-Mass; 670 (M+1)

$^1$H-NMR (DMSO-d$_6$):

δ (ppm); 0.70(d, 6H, J=6.8 Hz), 1.27(s, 9H), 1.40(s, 3H), 1.49(s, 3 H), 1.88–1.95(m, 1H), 2.5–2.8(m, 2H), 2.85(s, 6H), 4.13–4.24(m, 2H), 4.4–4.7(m, 4H), 4.89(d, 1H, J=8.9 Hz), 5.06–5.11(m, 2H), 6.20–6.23(m, 2H), 6.31–6.35(m, 1H), 7.0–7.2(m, 4H), 7.35(d, 2H, J=6.8 Hz), 7.58–7.67(m, 2H), 8–21(d, 1H, J=8.4 Hz)

Example 36

(R)-N-tert-butyl-3-{(2S,3S)-2-hydroxy-3-[(S)-2-(3-dimethylaminophenoxyacetyl)aminobutanoyl]amino-4-phenylbutanoyl}-5,5-dimethyl-1,3-thiazolidine-4-carboxamide ((3-Me$_2$N) Phoa-Abu-Apns-Dmt-NHtBu)

<Step 1>

(R)-N-tert-butyl-3-{(2S,3S)-2-hydroxy-3-[(S)-2-aminobutanoyl]amino-4-phenylbutanoyl}-5,5-dimethyl-1,3-thiazolidine-4-carboxamide (H-Abu-Apns-Dmt-NHtBu)

EDC.HCl (302 mg) was added to a solution of H-Apns-Dmt-NHtBu (619 mg), Boc-Abu-OH (305 mg), and HOBt (213 mg) in DMF (3 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was treated with 4N HCl/dioxane for two hours at room temperature. After concentration, the residue was dissolved in $H_2O$ and the mixture was washed with toluene. The aqueous layer neutralized with 2N NaOH was extracted with $CH_2Cl_2$, then the extract was washed with 5% NaCl and dried over $MgSO_4$. The dried material was filtered and concentrated to dryness to obtain the title compound (699 mg) was obtained.

<Process 2>

(R)-N-tert-butyl-3-{(2S,3S)-2-hydroxy-3-[(S)-2-(3-dimethylaminophenoxyacetyl)aminobutanoyl]amino-4-phenylbutanoyl}-5,5-dimethyl-1,3-thiazolidine-4-carboxamide (3-Me$_2$N) Phoa-Abu-Apns-Dmt-NHtBu)

3-dimethylaminophenoxyacetic acid (51 mg), HOBt (35mg), and EDC.HCl (53 mg) were added to a solution of H-Abu-Apns-Dmt-NHtBu (120 mg) obtained in the step 1 in DMF and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography to obtain the title compound (120 mg).

HPLC: 17.16 min

TOF-Mass; 656 (M+1)

$^1$H-NMR (DMSO-d6):

δ (ppm); 0.73 t, 3H, J=7.3 Hz), 1.27(s, 9H), 1.40(s, 3H), 1.49(s, 3H), 1.3–1.7(m, 2H), 2.5–2.8(m, 2H), 2.85(s, 6H), 4.1–4.3(m, 2H), 4.4–4.7(m, 4 H), 4.89(d, 1H, J=8.9 Hz), 5.04(d, 1H, J=8.9 Hz), 5.16(d, 1H, J=7.6 Hz), 6.20–6.23(m, 2H), 6.32–6.35(m, 1H), 7.0–7.2(m, 4H), 7.34(d, 2 H, J=7.3 Hz), 7.65–7.75(m, 2H), 8.19(d, 1H, J=8.1 Hz)

Example 37

(R)-N-(2-methylbenzyl)-3-{(2S,3S)-2-hydroxy-3-[(S)-2-methanesulfonylamino-3-methylbutanoyl]amino-4-phenylbutanoyl}-5,5-dimethyl-1,3-thiazolidine-4-carboxamide (Me-SO$_2$-Val-Apns-Dmt-NHBzl(2-Me))

Methanesulfonyl chloride (25 µl) and triethylamine (46 µl) were added to a solution of H-Val-Apns-Dmt-NHBzl(2-Me) (162 mg) in methylene chloride (3 ml) and the mixture was stirred for two hours. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography and reprecipitated from ethyl acetate/n-hexane to obtain the title compound (127 mg).

HPLC: 19.79 min

TOF-Mass; 619 (M+1)

Example 38

(R)-N-(2-methylbenzyl)-3-{(2S,3S)-2-hydroxy-3-[(S)-2-methanesulfonylaminobutanoyl]amino-4-phenylbutanoyl}-5,5-dimethyl-1,3-thiazolidine-4-carboxamide (Me-SO$_2$-Abu-Apns-Dmt-NHBzl(2-Me))

Methanesulfonyl chroride (25 µl) and triethylamine (46 µl) were added to a solution of H-Abu-Apns-Dmt-NHBzl (2-Me) (158 mg) in ethyl acetate (3 ml) and the mixture was stirred for two hours. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography and reprecipitated from ethyl acetate/n-hexane to obtain the title compound (92 mg).

HPLC: 19.08 min

TOF-Mass; 605 (M+1)

Example 39

(R)-N-(2-methylbenzyl)-3-{(2S,3S)-2-hydroxy-3-[N-(methoxycarbonyl)-L-threonyl]amino-4-phenylbutanoyl}-5,5-dimethyl-1,3-thiazolidine-4-carboxamide (MeO-CO-Thr-Apns-Dmt-NHBzl(2-Me))

Methyl chloroformate (39 µl) and triethylamine (70 µl) were added to a solution of H-Thr-Apns-Dmt-NHBzl(2-Me) (270 mg) in ethyl acetate (5 ml) and the mixture was stirred overnight. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography and reprecipitated from ethyl acetate/n-hexane to obtain the title compound (196 mg)

HPLC: 18.21 min

TOF-Mass; 601 (M+1)

Example 40

(R)-N-(2-methylbenzyl)-3-{(2S,3S)-2-hydroxy-3-[N-(methoxycarbonyl)-L-asparaginyl]amino-4-phenylbutanoyl}-5,5-dimethyl-1,3-thiazolidine-4-carboxamide (MeO-CO-Asn-Apns-Dmt-NHBzl(2-Me))

4N HCl/dioxane (2 ml) was added to the compound Boc-Asn-Apns-Dmt-NHBzl(2-Me) (70 mg) obtained in the step 1 of Example 6 and the mixture was stirred for two hours. After concentration, the reaction mixture was dissolved in DMF (1 ml) and neutralized with triethylamine (15 µl). After the addition of methyl chloroformate (9 µl ) and triethylamine (16 µl), the mixture was stirred for two hours. After the addition of ethyl acetate, the reaction mixture was washed with 3% $Na_2CO_3$, 1N HCl, and 5% NaCl and dried over $MgSO_4$. After filtration and concentration, the residue was purified using silica gel column chromatography to obtain the title compound (15 mg).

HPLC: 17.51 min

TOF-Mass; 614 (M+1)

Example 41

In order to verify that the tripeptide compound of the present invention has superior HIV protease inhibition activity and, in particular, is suitable for use as a medication because of its remarkably low inhibition constant to the HIV protease, the following experiments were performed.

Experimental Example 1

HIV Protease Inhibition Activity

In order to verify that the tripeptide compound of the present invention exhibits high HIV protease inhibition activity, the compounds of the Examples 1–38 were evaluated according to previously published experimental methods (see, for example, Journal of Synthetic Organic Chemistry Japan vol. 52, 403–412 (1994) and Japanese Patent Application Laid-open No. 170722/1993).

Experimental Method

The protease activity was measured using a recombinant HIV-1 protease (see Biochemistry, 250 (9)-264 (1990)) and a synthesized peptide substrate. The inhibition rate was calculated by determining a peptide fragment generated by cleavage between Tyr-Pro of the synthesized substrate after the reaction of 60 min at 37° C. using a reversed phase HPLC in the presence of the test compounds in various concentrations (see, for example, Japanese Patent Application Laid-open No. 170722/1993).

Examples of the evaluation results of the HIV protease inhibition activity of the tripeptide compound of the present invention by the above-described method is shown in Table 1. As shown in these results, each tripeptide compound of the present invention exhibits significantly high HIV protease inhibition activity. The concentration of the test compounds in Table 1 represents the final concentration in the reaction mixture.

TABLE 1

| Test compound | Abbreviated molecular formula | Enzyme activity inhibition rate (%) (addition concentration of 50 nM) |
|---|---|---|
| Example 1 | Z-Asn-Apns-Dmt-NHBzl | 96.0 |
| Example 2 | Z-Asn-Apns-Thz-NHBzl(2-Me) | 71.7 |
| Example 3 | Z-Asn-Apns-Dmt-NHBzl(2-Me) | 100.0 |
| Example 4 | Z-Val-Apns-Dmt-NHBzl(2-Me) | 95.3 |
| Example 5 | Z-Asn-Apns-Dmt-NHBzl(2-Cl) | 98.4 |
| Example 6 | Chc-Asn-Apns-Dmt-NHBzl(2-Me) | 98.4 |
| Example 7 | Bfc-Asn-Apns-Dmt-NHBzl(2-Me) | 91.2 |
| Example 8 | iQoa-Val-Apns-Dmt-NHBzl(2-Me) | 97.7 |
| Example 9 | Z-Asn-Apns-Mox-NHBzl(2-Me) | 61.9 |
| Example 10 | Bfc-Val-Apns-Dmt-NHBzl(2-Me) | 97.1 |
| Example 12 | Chc-Val-Apns-Dmt-NHBzl(2-Me) | 97.4 |
| Example 13 | 2-Quic-Val-Apns-Dmt-NHBzl(2-Me) | 96.6 |
| Example 14 | Btc-Val-Apns-Dmt-NHBzl(2-Me) | 95.8 |
| Example 15 | Bic-Val-Apns-Dmt-NHBZl(2-Me) | 92.8 |
| Example 16 | (7-MeO)Bfc-Val-Apns-Dmt-NHBzl(2-Me) | 97.1 |
| Example 17 | (3-Bzl)Phoa-Val-Apns-Dmt-NHBzl(2-Me) | 97.1 |
| Example 18 | 2-Qxc-Asn-Apns-Dmt-NHBzl(2-Me) | 98.8 |
| Example 19 | 2-Qxc-Val-Apns-Dmt-NHBzl(2-Me) | 97.3 |
| Example 20 | (7-MeO)Bfc-Ala-Apns-Dmt-NHBzl(2-Me) | 97.6 |
| Example 21 | 3-Quic-Val-Apns-Dmt-NHBzl(2-Me) | 97.7 |
| Example 22 | (3-Me$_2$N)Phoa-Val-Apns-Dmt-NHBzl(2-Me) | 97.6 |
| Example 23 | 5-Qoa-Val-Apns-Dmt-NHBzl(2-Me) | 98.5 |
| Example 24 | 6-Qoa-Abu-Apns-Dmt-NHBzl(2-Me) | 98.1 |
| Example 25 | (3-Me$_2$N)Phoa-Abu-Apns-Dmt-NHBzl(2-Me) | 99.9 |
| Example 26 | (3-Me$_2$N)Phoa-Ala-Apns-Dmt-NHBzl(2-Me) | 99.9 |
| Example 27 | MeO—CO-Val-Apns-Dmt-NHBzl(2-Me) | 94.9 |
| Example 28 | MeO—CO-Abu-Apns-Dmt-NHBzl(2-Me) | 93.6 |
| Example 29 | EtO—CO-Val-Apns-Dmt-NHBzl(2-Me) | 93.0 |
| Example 30 | MeO—(CH$_2$)$_2$—O—CO-Val-Apns-Dmt-NHBzl(2-Me) | 94.2 |
| Example 31 | MeO—CH$_2$—CO-Val-Apns-Dmt-NHBzl(2-Me) | 89.6 |
| Example 32 | EtO—CH$_2$—CO-Val-Apns-Dmt-NHBzl | 96.4 |
| Example 33 | Ac-Val-Apns-Dmt-NHBzl(2-Me) | 89.8 |
| Example 34 | Ac-Abu-Apns-Dmt-NHBzl(2-Me) | 88.9 |
| Example 35 | (3-Me$_2$N)Phoa-Val-Apns-Dmt-NHtBu | 96.0 |
| Example 36 | (3-Me$_2$N)Phoa-Abu-Apns-Dmt-NHtBu | 95.0 |
| Example 37 | Me—SO$_2$-Val-Apns-Dmt-NHBzl(2-Me) | 70.1 |
| Example 38 | Me—SO$_2$-Abu-Apns-Dmt-NHBzl(2-Me) | 76.0 |
| Example 39 | MeO—CO-Thr-Apns-Dmt-NHBzl(2-Me) | 84.6 |
| Example 40 | MeO—CO-Asn-Apns-Dmt-NHBzl(2-Me) | 94.3 |

Experimental Example 2

Evaluation of Enzyme Inhibition Constant Ki

The enzyme inhibition constant Ki was evaluated in order to verify that the tripeptide compound of the present invention exhibits a markedly superior inhibition ability compared with a conventional tripeptide type inhibition substance. In addition, the known compound KNI-162 for which high HIV protease inhibition activity has been reported to publications (see, for example, Yoshiaki Kiso, Journal of Synthetic Organic Chemistry Japan vol. 52, 403–412 (1994)) was similarly tested for comparison. This compound KNI-162: (R) 3{(2S,3S)-3-[N-(benzyloxycarbonyl)-L-asparaginyl]amino-2-hydroxy-4-phenylbutanoyl}-5,5-dimethyl-1,3-thiazolidine-4-carboxamide is a hydroxymethylcarboxamide type tripeptide compound having a (2S,3S)-3-amino-2-hydroxy-4-phenylbutanoyl skeleton which is similar to the tripeptide compound of the present invention except that the tert-butyl group is substituted on the C-terminal amide nitrogen atom.

Experimental Method

The synthesized peptide substrate having a sequence of H-Lys-Ala-Arg-Val-Tyr-Phe (4-NO$_2$)-Glu-Ala-Nle-NH$_2$ (SEQ ID NO. 1) was used in this experiment. The enzyme reaction was measured using a reversed phase HPLC by determining the C-terminal peptide fraction produced by cleavage just behind Tyr in the synthesized substrate which is obtained by reacting the following composition for 15 min. at 37° C. and stopping the reaction by the addition of 1N HCl (75 μl).

| Composition of reaction mixture | |
|---|---|
| Recombinant HIV-1 protease enzyme solution | 10 μl |
| 0.5 mM synthetic substrate aqueous solution | 10 μl |
| DMSO Inhibitor solution | 5 μl |
| 0.2 M MES solution (1 M NaCl, 2 mM EDTA-2Na, 2 mM DTT, pH 5.5) | 25 μl |

Reversed Phase HPLC Measurement Conditions
Column: Waters Nova-pak C18 (3.9×75 mm)
Eluent: A; water (0.1% TFA)

B; acetonitrile (0.1% TFA)
Flow rate: 2 ml/min isocratic; 10% B solution
Detection: Fluorescence 305 nm, excitation 275 nm Examples of the evaluation of the enzyme inhibition constant Ki are shown in Table 2. In addition to the above compound KNI-162, the enzyme inhibition constant Ki of Saquinavir (Ro31-8959) and Ritonavir (ABT-538) which is sold at a market as the HIV protease inhibitors are also shown in Table 2 for comparison. In addition, the enzyme inhibition constant Ki was calculated after the addition of the test compound to the above-mentioned enzyme reaction system in the range of the final concentration of 1–100 nM, by fitting the relation between concentration of the test compound and the residual enzyme activity to the following numerical formula (1) according to the reversible tight-binding inhibitor model. However, the Michaelis constant was separately calculated.

$$V = \frac{1 V_0}{2Et}\left(\left\{\left[\left(1 + \frac{S}{Km}\right) + It - Et\right]^2 + 4Ki\left(1 + \frac{S}{Km}\right)Et\right\}^{\frac{1}{2}} - \left[Ki\left(1 + \frac{S}{Km}\right) + It - Et\right]\right) \quad (1)$$

VO: Initial flow rate
Km: Michaelis constant
S: Substrate concentration
Et: Active enzyme concentration
It: Inhibitor concentration

TABLE 2

| Test compound | Abbreviated molecular formula | Enzyme inhibition constant Ki |
|---|---|---|
| Example 1 | Z-Asn-Apns-Dmt-NHBzl | 19 |
| Example 6 | Chc-Asn-Apns-Dmt-NHBzl(2-Me) | 1.7 |
| Example 7 | Bfc-Asn-Apns-Dmt-NHBzl(2-Me) | 4.8 |
| Example 3 | Z-Asn-Apns-Dmt-NHBzl(2-Me) | 16 |
| Example 16 | (7-MeO)-Bfc-Val-Apns-Dmt-NHBzl(2-Me) | 14 |
| Example 28 | MeO—CO-Abu-Apns-Dmt-NHBzl(2-Me) | 242 |
| Example 35 | (3-Me$_2$N)-Phoa-Val-Apns-Dmt-NhtBu | 70 |
| Example 36 | (3-Me$_2$N)-Phoa-Abu-Apns-Dmt-NhtBu | 130 |
| KNI-162 (Reference Example) | Z-Asn-Apns-Dmt-NHt-Bu | 212 |
| Saquinavir (Ro31-8959) | | 138 |
| Ritonavir (ABT-538) | | 98 |

As shown in Table 2, the enzyme inhibition constant Ki of the tripeptide compound of the present invention exhibits remarkably low values. Specifically, it is recognized that the tripeptide compound of the present invention has a remarkably high binding affinity with the HIV protease. Moreover, compared with the compound KNI-162 of the Reference Example, it is judged that the tripeptide compound of the present invention exhibits remarkably superior HIV protease inhibition activity. It is considered that the increase of the binding affinity of the tripeptide compound of the present invention is mainly caused by the C-terminal substituted benzyl amide.

Experimental Example 3

Evaluation of Anti-HIV Activity and Cytotoxicity

In order to verify that the tripeptide compound of the present invention excels in the effect of inhibiting production of the HIV virus particles in the host cell owing to the remarkably superior HIV protease inhibition compared with the conventional tripeptide type inhibition substance, the following anti-HIV activity evaluation tests were carried out. At the same time, 50% cytotoxic concentration was evaluated in order to identify the degree of cytotoxicity. In addition, Ritonavir which is sold at a market peptide type HIV protease inhibition substance, was also evaluated for comparison.

Experimental Method for Anti-HIV Activity and Cytotoxicity

According to a method which has already been reported to publications and the like (Weislowet. al., J. of the National Cancer Institute, 81, 577–585 (1989)), the anti-HIV activity was evaluated using a CEM-SS cell as the host cell and the HIV virus strain HIV-1 IIIB (see, for example, the European Patent Publication No. EP 0751145 A2).

On a 96-well micro titre plate, the test compounds were added to the culture medium in various concentrations, then the HIV infected CEM-SS cell was added and incubated for six days at 37° C. using a $CO_2$ incubator. The number of the living cells was then measured by a XTT method. On the other hand, in order to examine the cytotoxicity of the test compounds, the test compounds were added in various concentrations and the HIV virus non-infected cell was incubated under similar conditions. As the reference group, the HIV infected CEM-SS cell was incubated without the addition of the test compounds. Moreover, the HIV virus non-infected cell was incubated without the addition of the test compound as the control group.

The anti-virus activity was evaluated in a concentration in which the cytotoxic effect caused by the HIV infected virus in the above HIV infected cell group was inhibited 50 percent ($EC_{50}$, 50% effective concentration), and the cytotoxicity was evaluated in a concentration in which the cytotoxic effect by the addition of the test compound in the HIV virus non-infected cell group occurred at 50 percent ($TC_{50}$, 50% cytotoxic concentration) respectively. In addition, since no cytotoxic effect was seen even at the highest concentration (1.0 μg/ml) in this experiment, the value of $TC_{50}$ was described as >1.0 μg/ml. Examples of the evaluation results are shown in Table 3.

TABLE 3

| Test compound | Anti-virus activity $EC_{50}$ (ng/ml) | Cytotoxicity $TC_{50}$ (μg/ml) |
|---|---|---|
| Example 16 | 1.7 | >1.0 |
| Example 27 | 26 | >1.0 |
| Example 35 | 10 | >1.0 |
| Example 36 | 17 | >1.0 |
| Ritonavir (Reference Example) | 33 | >1.0 |

As shown in Table 3, the tripeptide compound of the present invention exhibits the anti-virus activity in markedly low concentrations corresponding to the significantly small values of the enzyme inhibition constant Ki. On the other hand, the cytotoxicity is only shown in concentrations three digits or more in the range of concentration in which the anti-virus activity is exhibited. Moreover, there is no significant difference in toxicity between the tripeptide compound of the present invention and Ritonavir which is sold at a market compound.

Experimental Example 4

Pharmacokinetics Test (Evaluation of Digestive Tract Absorption and Metabolic Characteristics)

The metabolic characteristics of the tripeptide compound of the present invention were evaluated using rats for a test animal. As the Control Example, the result of KNI-272 ((R)-N-tert-butyl-3-{(2S,3S)-2-hydroxy-3-[N-(isoquinolin-5-yloxy)acetyl-methylthio-L-alanyl]amino-4-phenylbutanoyl}-1,3-thiazolidine-4-carboxamide; iQoa-Mta-Apns-Thz-NHtBu) which is a tripeptide derivative known in the art, is also shown. The amount administred was 10 mg/kg. The evaluated administration methods are a method (id) of administering a solution of a fixed amount of the test compound in the duodenum of a test animal, and a method (iv) of administering the solution intravenously. After administration, blood samples were taken from the test animal and concentrations of the residual test compound in the plasma were analyzed. As indices concerning pharmacokinetics, AUC (area under medicine concentration curve in plasma), MRT (mean residence time), $t_{1/2}(\lambda)$ (final phase half-life period), and the biological utilization rate of administration in the duodenum F were calculated. The results are shown in Table 4.

TABLE 4

| Test compound | Administration | AUC (μg/ml · min.) | MRT (min.) | T½ (λ) (min.) | F (%) |
|---|---|---|---|---|---|
| Example 16 | Iv | 322 | 67 | 74 | — |
|  | Id | 90 |  |  | 27 |
| Example 27 | Iv | 272 | 71 | 87 | — |
|  | Id | 87 |  |  | 32 |
| Example 35 | Iv | 119 | 68 | 63 | — |
|  | Id | 105 |  |  | 89 |
| Example 36 | Iv | 226 | 124 | 110 | — |
|  | Id | 185 |  |  | 82 |
| KNI-272 (Reference Example) | Iv | 224 | 23 | 26 | — |
|  | Id | 98 |  |  | 43 |

As shown in these results, each tripeptide compound of the present invention has superior stability in vivo and is able to maintain high concentration in plasma compared with KNI- 272 which is the compound of the Control Example.

Example 42

A granular agent was prepared according to the method of Japanese Patent Application Laid-open No. 208478/1996 using the tripeptide compound of the present invention as the effective component. One of the examples is given below.

Chc-Asn-Apns-Dmt-NHBzl(2-Me) (50 g) obtained in Example 6 and hydroxypropyl methylcellulose 2910 (binder) (20 g) were dissolved in a mixture (930 g) of ethanol (The Pharmacopoeia of Japan) (837 g) and purified water (93 g) to adjust the total weight to 1000 g. The resulting solution was used as a coating solution. True spherical particles with a diameter of 150–300 μm, Cellphia CP203 (500 g) (trademark: manufactured by Asahi Chemical Industry Co., Ltd.), was used as a core material. The particles were fed to a rolling-type fluidized bed coating apparatus Multiplex (trademark: manufactured by Paureck Co., Ltd.) under the conditions of air feed temperature of 55° C. and air flow rate of 40 m³/hr. The above coating solution was sprayed and dried to form a coating layer on the core material particles. These coating particles were sieved using a 42-mesh sieve and the particles which passed through were used as the granular agent.

INDUSTRIAL APPLICABILITY

The tripeptide compound of the present invention which is represented by the general formula (I) exhibits peculiar and remarkably high HIV protease inhibition activity, because not only the dipeptide moiety part which is indispensable for the HIV protease inhibition activity, but also the substituted benzyl group on the C-terminal amide nitrogen atom participate in binding to the enzyme active center of the HIV protease. Therefore, when used for clinical application as an anti-AIDS medicine, there is the advantage that the amount to be administered to obtain the desired concentration of the peptide compound, which is the effective component for producing the desired medical effect, can be decreased. Moreover, since the tripeptide compound which is represented by the general formula. (III) exhibits peculiar and remarkably high HIV protease inhibition activity as well as high digestive tract absorption, when used for a clinical application as the anti-AIDS medicine, there is the advantage that the amount to be administered to obtain the desired concentration of the peptide compound, which is the effective component for producing the desired medical effect, can be decreased.

What is claimed is:

1. A compound having the following formula (I),

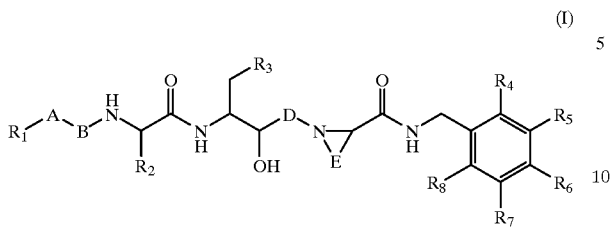

wherein
A is —NH—, —NR— (wherein R represents an alkyl group having 1 to 6 carbon atoms), —O—CH$_2$—, —CH$_2$—O— or a single bond;
B is —CO— or —SO$_2$—;
D is —CO— or —CH$_2$—;
E represents
i) a divalent hydrocarbon chain —(CH$_2$)$_n$— wherein n is an integer ranging from 3 to 5, wherein E forms a 5 to 7 member ring together with the adjacent nitrogen atom and carbon atom, and wherein one or more carbon atom positions of E are replaced by one or more nitrogen, oxygen or sulfur atoms, or
ii) a divalent hydrocarbon chain as described in i) above further comprising 2 or more substituents, said substituents being selected from the group consisting of
a linear and branched aliphatic hydrocarbon group having 1 to 6 carbon atoms, aromatic hydrocarbon group, heteroaromatic group, hydroxyl group, linear and branched aliphatic hydrocarbonoxy group having 1 to 6 carbon atoms and halogeno group, wherein said substituents optionally form a another condensed 5 to 7 member ring;
$R^1$ is i) a hydrogen atom,
ii) an alkyl group having 1 to 6 carbon atoms, wherein the said alkyl group is optionally substituted by an alkyloxy group having 1 to 4 carbon atoms, or
iii) an aromatic group, a heterocyclic group, said aromatic and said heterocyclic groups having 1 to 10 carbon atoms and being optionally substituted by an alkyl group having 1 to 4 carbon atoms,
an hetero alkyl group selected from
alkyloxy group, mono or dialkyl-substituted amino group, wherein the alkyl group has 1–4 carbon atoms,
halogeno group, hydroxyl group, amino group, or
an alkyl or alkenyl group having 3 or less carbon atoms which may be substituted by a monocyclic aromatic group or monocyclic heteroaromatic group;
$R^2$ is i) a linear or branched aliphatic hydrocarbon group having 1–7 carbon atoms,
ii) an aromatic hydrocarbon group,
iii) said aliphatic hydrocarbon group or aromatic hydrocarbon group of i) and ii) further comprising a hetero atom in place of a carbon atom, or
iv) said aliphatic hydrocarbon group or aromatic hydrocarbon group of i) to iii) wherein a hydrogen atom is substituted by a carbamoyl group, carboxyl group, or halogeno group;
$R^3$ is an aryl group, arylthio group or aryloxy group, and wherein the aryl moiety is optionally substituted by 1 to 2 of the substituents selected from the group consisting of
an alkyl, alkyloxy group, and alkylamino group, wherein the alkyl moiety is an alkyl group of 1 to 4 carbon atoms,
a halogeno group, hydroxyl group, and amino group; and
$R^4$, $R^5$, $R^6$, $R^7$ and $R^8$ respectively represent a hydrogen atom, alkyl group having 1 to 3 carbon atoms, halogeno group, amino group, hydroxyl group, aminomethyl group, hydroxymethyl group, or an amino group substituted by one or two alkyl groups having 1 to 3 carbon atoms; or
a pharmaceutically acceptable salt thereof.

2. A compound having the following formula (II)

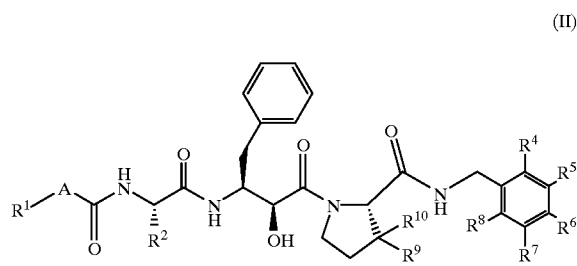

wherein A is —NH—, —NR— (wherein R represents an alkyl group having 1 to 6 carbon atoms), —O—CH$_2$—, —CH$_2$—O— or a single bond;
X is an oxygen atom or sulfur atom;
$R^1$ is i) a hydrogen atom,
ii) an alkyl group having 1 to 6 carbon atoms, wherein the said alkyl group is optionally substituted by an alkyloxy group having 1 to 4 carbon atoms, or
iii) an aromatic group, a heterocyclic group, said aromatic and said heterocyclic groups having 1 to 10 carbon atoms and being optionally substituted by an alkyl group having 1 to 4 carbon atoms,
an hetero alkyl group selected from
alkyloxy group, mono or dialkyl-substituted amino group, wherein the alkyl group has 1–4 carbon atoms,
halogeno group, hydroxyl group, amino group, or
an alkyl or alkenyl group having 3 or less carbon atoms which may be substituted by a monocyclic aromatic group or monocyclic heteroaromatic group;
$R^2$ is i) a linear or branched aliphatic hydrocarbon group having 1–7 carbon atoms,
ii) an aromatic hydrocarbon group,
iii) said aliphatic hydrocarbon group or aromatic hydrocarbon group of i) and ii) further comprising a hetero atom in place of a carbon atom, or
iv) said aliphatic hydrocarbon group or aromatic hydrocarbon group of i) to iii) wherein a hydrogen atom is substituted by a carbamoyl group, carboxyl group, or halogeno group;
$R^4$, $R^5$, $R^6$, $R^7$ and $R^8$ respectively represent a hydrogen atom, alkyl group having 1 to 3 carbon atoms, halogeno group, amino group, hydroxyl group, aminomethyl group, hydroxymethyl group, or an amino group substituted by one or two alkyl groups having 1 to 3 carbon atoms; and
$R^9$ and $R^{10}$ respectively represents a hydrogen atom or a linear, or branched, aliphatic hydrocarbon group having 1 to 6 carbon atoms; or
a pharmaceutically acceptable salt thereof.

3. The compound according to claim 2 or a pharmaceutically acceptable salt thereof, wherein
A is —O—CH$_2$—, —CH$_2$—O—, or a single bond;
X is a sulfur atom; and
R$^4$ or R$^8$ is an alkyl group having 1 to 3 carbon atoms, halogeno group, amino group, hydroxyl group, aminomethyl group, hydroxymethyl group, or an amino group substituted by one or two alkyl groups having 1 to 3 carbon atoms.

4. The compound according to claim 2 or a pharmaceutically acceptable salt thereof, wherein
X is a sulfur atom;
R$^9$ and R$^{10}$ are methyl groups; and
R$^4$ or R$^8$ is alkyl group having 1 to 3 carbon atoms, halogeno group, amino group, hydroxyl group, aminomethyl group, hydroxymethyl group, or an amino group substituted by one or two alkyl groups having 1 to 3 carbon atoms.

5. The compound according to claim 2 or a pharmaceutically acceptable salt thereof, wherein
A is —O—CH$_2$—, —CH$_2$—O—, or a single bond;
X is a sulfur atom;
R$^9$ and R$^{10}$ are methyl groups;
R$^1$ is an aromatic group, an heterocyclic group, said aromatic and said heterocyclic groups having 1 to 10 carbon atoms and being optionally substituted by
an alkyl group having 1 to 4 carbon atoms,
an hetero alkyl group selected from
alkyloxy group, mono or dialkyl-substituted amino group, wherein the alkyl group has 1–4 carbon atoms, halogen group, hydroxyl group, amino group, or
an alkyl or alkenyl group having 3 or less carbon atoms which may be substituted by a monocyclic aromatic group or monocyclic heteroaromatic group;
R$^2$ is a methyl, ethyl, propyl, isopropyl, carbamoylmethyl, or methylthiomethyl group; and;
R$^4$ or R$^8$ is alkyl group having 1 to 3 carbon atoms, halogeno group, amino group, hydroxyl group, aminomethyl group, hydroxymethyl group, or an amino group substituted by one or two alkyl groups having 1 to 3 carbon atoms.

6. The compound according to claim 2 or a pharmaceutically acceptable salt thereof, wherein
A is —O—CH$_2$—, —CH$_2$—O—, or a single bond;
X is a sulfur atom;
R$^9$ and R$^{10}$ are methyl groups;
R$^1$is an aromatic group, an heterocyclic group, said aromatic and said heterocyclic groups having 1 to 10 carbon atoms and being optionally substituted by
an alkyl group having 1 to 4 carbon atoms,
a hetero alkyl group selected from alkyloxy group and monoalkyl- and dialkyl-substituted amino group, wherein the alkyl group has 1–4 carbon atoms,
halogen group, hydroxyl group, amino group, or
an alkyl or alkenyl group having 3 or less carbon atoms which may be substituted by a monocyclic aromatic group or monocyclic heteroaromatic group;
R$^2$ is a methyl, ethyl, propyl, isopropyl, carbamoylmethyl, or methylthiomethyl group;
R$^4$ is a methyl, ethyl, or halogeno group; and
R$^5$, R$^6$, R$^7$, and R$^8$ are hydrogen atoms.

7. The compound according to claim 2 or a pharmaceutically acceptable salt thereof, represented by the formula (VI),

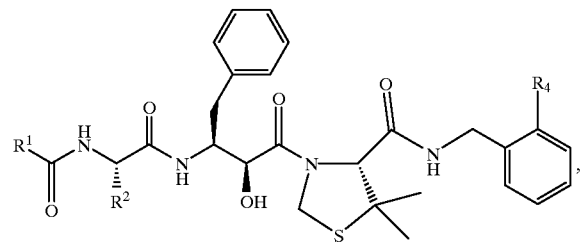

wherein R$^1$ is i) a hydrogen atom,
ii) an alkyl group having 1 to 6 carbon atoms, wherein the said alkyl group is optionally substituted by an alkyloxy group having 1 to 4 carbon atoms, or
iii) an aromatic group, a heterocyclic group, said aromatic and said heterocyclic groups having 1 to 10 carbon atoms and being optionally substituted by
an alkyl group having 1 to 4 carbon atoms,
a hetero alkyl group selected from alkyloxy group, and monoalkyl- or dialkyl-substituted amino group, wherein the alkyl group has 1–4 carbon atoms,
halogen group, hydroxyl group, amino group, or
an alkyl or alkenyl group having 3 or less carbon atoms which may be substituted by a monocyclic aromatic group or monocyclic heteroaromatic group;
R$^2$ is a methyl, ethyl, propyl, isopropyl, carbamoylmethyl, or methylthiomethyl group; and
R$^4$ is a methyl, ethyl, or halogeno group.

8. The compound according to claim 2 or a pharmaceutically acceptable salt thereof, represented by formula (VII),

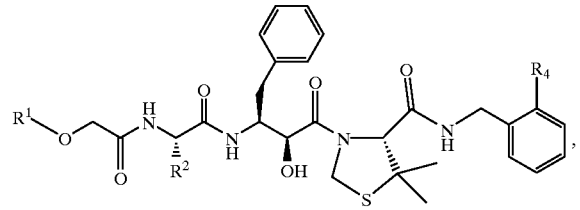

wherein R$^1$ is i) a hydrogen atom,
ii) an alkyl group having 1 to 6 carbon atoms, wherein the said alkyl group is optionally substituted by an alkyloxy group having 1 to 4 carbon atoms, or
iii) an aromatic group, a heterocyclic group, said aromatic and said heterocyclic groups having 1 to 10 carbon atoms and being optionally substituted by
an alkyl group having 1 to 4 carbon atoms,
a hetero alkyl group selected from alkyloxy group, and monoalkyl- or dialkyl-substituted amino group, wherein the alkyl group has 1–4 carbon atoms,
halogen group, hydroxyl group, amino group, or
an alkyl or alkenyl group having 3 or less carbon atoms which may be substituted by a monocyclic aromatic group or monocyclic heteroaromatic group;
R$^2$ is a methyl, ethyl, propyl, isopropyl, carbamoylmethyl, or methylthiomethyl group; and $R^4$ is a methyl, ethyl, or halogeno group.

9. The compound according to claim 2 or a pharmaceutically acceptable salt thereof, represented by formula (VIII),

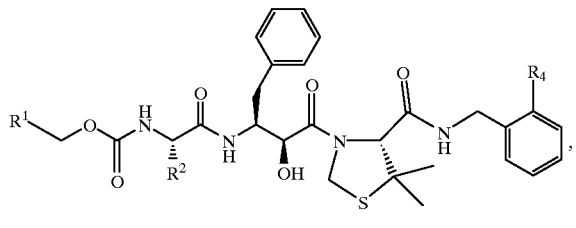

(VIII)

wherein $R^1$ is i) a hydrogen atom,
ii) an alkyl group having 1 to 6 carbon atoms, wherein the said alkyl group is optionally substituted by an alkyloxy group having 1 to 4 carbon atoms, or
iii) an aromatic group, a heterocyclic group, said aromatic and said heterocyclic groups having 1 to 10 carbon atoms and being optionally substituted by
an alkyl group having 1 to 4 carbon atoms,
a hetero alkyl group selected from alkyloxy group, and monoalkyl- or dialkyl-substituted amino group, wherein the alkyl group has 1–4 carbon atoms,
halogen group, hydroxyl group, amino group, or
an alkyl or alkenyl group having 3 or less carbon atoms which may be substituted by a monocyclic aromatic group or monocyclic heteroaromatic group;

$R^2$ is a methyl, ethyl, propyl, isopropyl, carbamoylmethyl, or methylthiomethyl group; and $R^4$ is a methyl, ethyl, or halogeno group.

10. The compound of claim 1 having the formula:

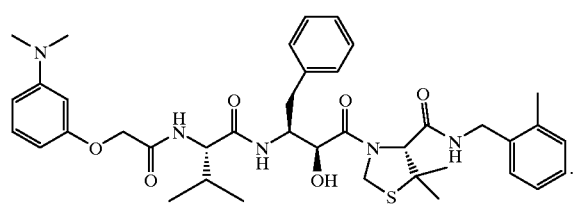

11. A composition for the treatment of HIV infection, comprising an effective anti-HIV amount of a compound according to claim 1 or a pharmaceutically acceptable salt thereof.

12. A composition for the treatment of HIV infection, comprising an effective anti-HIV amount of a compound according to claim 2 or a pharmaceutically acceptable salt thereof.

13. A composition for the treatment of HIV infection, comprising an effective anti-HIV amount of a compound according to claim 10 or a pharmaceutically acceptable salt thereof.

14. A method of inhibiting HIV protease comprising contacting said protease with an effective inhibitory amount of a compound according to claim 1.

15. A method of inhibiting HIV protease, comprising contacting said protease with an effective inhibitory amount of a compound according to claim 2.

16. A method of inhibiting HIV protease, comprising contacting said protease with an effective inhibitory amount of a compound according to claim 10.

17. The compound of claim 1 having the following formula (I'):

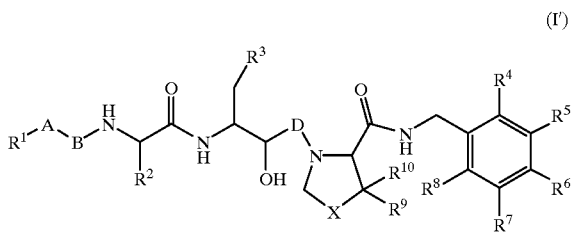

(I')

wherein $R^1$ to $R^8$, A, B, and D are as defined in claim 12,
X is an oxygen atom or a sulfur atom, and
$R^9$ and $R^{10}$ each independently represents a hydrogen atom or a linear or branched aliphatic hydrocarbon group having 1 to 6 carbon atom; or a pharmaceutically acceptable salt thereof.

18. The compound of claim 17, wherein X is a sulfur atom and wherein $R^9$ and $R^{10}$ are hydrogen.

19. The compound of claim 17, wherein X is a sulfur atom and wherein $R^9$ and $R^{10}$ are methyl.

20. A composition for the treatment of HIV infection, comprising an effective anti-HIV amount of a compound according to claim 17 or a pharmaceutically acceptable salt thereof.

21. A method of inhibiting HIV protease comprising contacting said protease with an effective inhibitory amount of a compound according to claim 17.

22. A compound having the following formula (I),

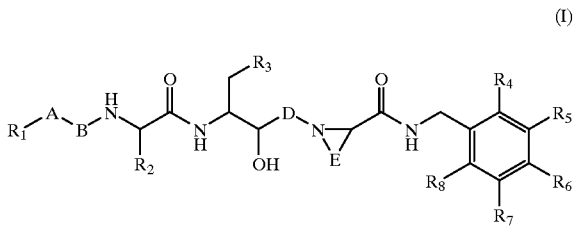

(I)

wherein

A is —NH—, —NR — (wherein R represents an alkyl group having 1 to 6 carbon atoms), —O—CH$_2$—, —CH$_2$—O— or a single bond;

B is —CO— or —SO$_2$—;

D is —CO— or —CH$_2$—;

E represents
i) a divalent hydrocarbon chain —(CH$_2$)$_1$— wherein n is an integer ranging from 3 to 5, wherein E forms a 5 to 7 member ring together with the adjacent nitrogen atom and carbon atom, and wherein one or more carbon atom positions of E are replaced by one or more nitrogen, oxygen or sulfur atoms, or
ii) a divalent hydrocarbon chain as described in i) above further comprising 2 or more substituents, said substituents being selected from the group consisting of a linear and branched aliphatic hydrocarbon group having 1 to 6 carbon atoms, aromatic hydrocarbon group, heteroaromatic group, hydroxyl group, linear and branched aliphatic hydrocarbonoxy group having 1 to 6 carbon atoms and halogeno group, wherein said substituents optionally form a another condensed 5 to 7 member ring;

R is i) a hydrogen atom,
  ii) an alkyl group having 1 to 6 carbon atoms, wherein the said alkyl group is optionally substituted by an alkyloxy group having 1 to 4 carbon atoms, or
  iii) an aromatic group, a heterocyclic group, said aromatic and said heterocyclic groups having 1 to 10 carbon atoms and being optionally substituted by an alkyl group having 1 to 4 carbon atoms,
    an hetero alkyl group selected from
      alkyloxy group, mono or dialkyl-substituted amino group, wherein the alkyl group has 1–4 carbon atoms,
      halogeno group, hydroxyl group, amino group, or
      an alkyl or alkenyl group having 3 or less carbon atoms which may be substituted by a monocyclic aromatic group or monocyclic heteroaromatic group;

$R^2$ is i) a linear or branched aliphatic hydrocarbon group having 1–7 carbon atoms,
  ii) an aromatic hydrocarbon group,
  iii) said aliphatic hydrocarbon group or aromatic hydrocarbon group of i) and ii) further comprising a hetero atom in place of a carbon atom, or
  iv) said aliphatic hydrocarbon group or aromatic hydrocarbon group of i) to iii) wherein a hydrogen atom is substituted by a carbamoyl group, carboxyl group, or halogeno group;

$R^3$ is an aryl group, arylthio group or aryloxy group, and wherein the aryl moiety is optionally substituted by 1 to 2 of the substituents selected from the group consisting of
  an alkyl, alkyloxy group, and alkylamino group, wherein the alkyl moiety is an alkyl group of 1 to 4 carbon atoms,
  a halogeno group, hydroxyl group, and amino group; and $R^4$, $R^5$, $R^6$, $R^7$ and $R^8$ respectively represent a hydrogen atom, alkyl group having 1 to 3 carbon atoms, halogeno group, amino group, hydroxyl group, aminomethyl group, hydroxymethyl group, or an amino group substituted by one or two alkyl groups having 1 to 3 carbon atoms, wherein at least one of $R^4$, $R^5$, $R^6$, $R^7$ and $R^8$ is not a hydrogen atom; or
a pharmaceutically acceptable salt thereof.

23. A compound having the following formula (II)

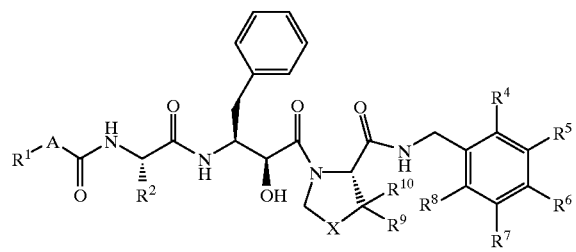

(II)

wherein A is —NH—, —NR— (wherein R represents an alkyl group having 1 I to 6 carbon atoms), —O—$CH_2$—, —$CH_2$—O— or a single bond;

X is an oxygen atom or sulfur atom;

$R^1$ is i) a hydrogen atom,
  ii) an alkyl group having 1 to 6 carbon atoms, wherein the said alkyl group is optionally substituted by an alkyloxy group having 1 to 4 carbon atoms or
  iii) an aromatic group, a heterocyclic group, said aromatic and said heterocyclic groups having 1 to 10 carbon atoms and being optionally substituted by an alkyl group having 1 to 4 carbon atoms,
    an hetero alkyl group selected from
      alkyloxy group, mono or dialkyl-substituted amino group, wherein the alkyl group has 1–4 carbon atoms,
    halogeno group, hydroxyl group, amino group, or an alkyl or alkenyl group having 3 or less carbon atoms which may be substituted by a monocyclic aromatic group or monocyclic heteroaromatic group;

$R^2$ is i) a linear or branched aliphatic hydrocarbon group having 1–7 carbon atoms.
  ii) an aromatic hydrocarbon group,
  iii) said aliphatic hydrocarbon group or aromatic hydrocarbon group of i) and ii) further comprising a hetero atom in place of a carbon atom, or
  iv) said aliphatic hydrocarbon group or aromatic hydrocarbon group of i) to iii) wherein a hydrogen atom is substituted by a carbamoyl group, carboxyl group, or halogeno group;

$R^4$, $R^5$, $R^6$, $R^7$ and $R^8$ respectively represent a hydrogen atom, alkyl group having 1 to 3 carbon atoms, halogeno group, amino group, hydroxyl group, aminomethyl group, hydroxymethyl group, or an amino group substituted by one or two alkyl groups having 1 to 3 carbon atoms, wherein at least one of $R^4$, $R^5$, $R^6$, $R^7$ and $R^8$ is not a hydrogen atom; and $R^9$ and $R^{10}$ respectively represents a hydrogen atom or a linear, or branched, aliphatic hydrocarbon group having 1 to 6 carbon atoms; or
a pharmaceutically acceptable salt thereof.

* * * * *